US005804581A

United States Patent [19]
Wolanin

[11] Patent Number: 5,804,581
[45] Date of Patent: Sep. 8, 1998

[54] INHIBITION OF MATRIX METALLOPROTEASES BY SUBSTITUTED PHENALKYL COMPOUNDS

[75] Inventor: Donald J. Wolanin, Orange, Conn.

[73] Assignee: Bayer Corporation, Pittsburgh, Pa.

[21] Appl. No.: 856,696

[22] Filed: May 15, 1997

[51] Int. Cl.⁶ ...................... A61K 31/195; A61K 31/535; C07D 295/13; C07D 295/192
[52] U.S. Cl. ..................... 514/237.5; 514/237.8; 514/533; 514/563; 344/169; 344/171; 560/39; 560/41; 562/442; 562/444; 562/449; 562/450
[58] Field of Search ..................... 544/169, 171; 560/41; 562/442; 514/237.5

[56] References Cited

PUBLICATIONS

Kluender et al, Chemical Abstracts, vol. 125, No. 142275 (1997).

International Search Report, International Application No. PCT/US 97/07919.

Rasmussen and MCCann, Pharmacol. Ther., 75 69–75 (1997).

Conway, et al., Clin. Exp. Metastasis, 14, 115–124 (1996).

Santos, et al., Clin. Exp. Metastasis, 15, 499–508 (1997).

*Primary Examiner*—Robert W. Ramsuer

[57] ABSTRACT

Matrix metalloprotease inhibiting compounds, pharmaceutical compositions thereof and a method of disease treatment using such compounds are presented. The compounds of the invention have the generalized formula:

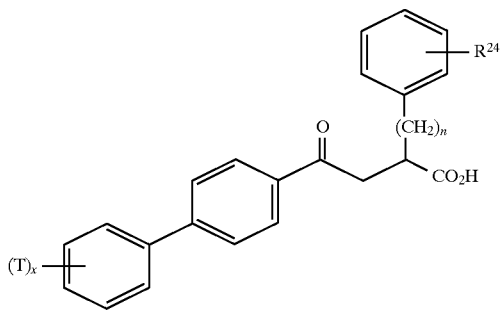

wherein T is a substituent and $R^{24}$ is a substituted amide moiety.

These compounds are useful for inhibiting matrix metalloproteases and, therefore, combating conditions to which MMP's contribute, such as osteoarthritis, rheumatoid arthritis, septic arthritis, periodontal disease, corneal ulceration, proteinuria, aneurysmal aortic disease, dystrophobic epidermolysis, bullosa, conditions leading to inflammatory responses, osteopenias mediated by MMP activity, tempera mandibular joint disease, demyelating diseases of the nervous system, tumor metastasis or degenerative cartilage loss following traumatic joint injury, and coronary thrombosis from athrosclerotic plaque rupture. The present invention also provides pharmaceutical compositions and methods for treating such conditions.

7 Claims, No Drawings

INHIBITION OF MATRIX METALLOPROTEASES BY SUBSTITUTED PHENALKYL COMPOUNDS

This patent application claims priority from U.S. provisional application, which was converted from U.S. application Ser. No. 08/645,026, filed May 15, 1996, to a provisional application by a petition under 37 C.F.R. §1.53(b) (2) (ii) filed on May 14, 1997.

BACKGROUND OF THE INVENTION

1. Field of the Invention

This invention relates to enzyme inhibitors, and more particularly, to novel substituted phenethyl compounds or derivatives thereof useful for inhibiting matrix metalloproteases.

2. Description of the Related Art

The matrix metalloproteases (a.k.a. matrix metalloendoproteinases or MMPs) are a family of zinc endoproteinases which include, but are not limited to, interstitial collagenase (a.k.a., MMP-1), stromelysin (a.k.a., proteoglycanase, transin, or MMP-3), gelatinase A (a.k.a., 72 kDa-gelatinase or MMP-2) and gelatinase B (a.k.a., 95 kDa-gelatinase or MMP-9). These MMPs are secreted by a variety of cells including fibroblasts and chondrocytes, along with natural proteinaceous inhibitors known as TIMPs (Tissue Inhibitor of MetalloProteinase).

All of these MMPs are capable of destroying a variety of connective tissue components of articular cartilage or basement membranes. Each MMP is secreted as an inactive proenzyme which must be cleaved in a subsequent step before it is able to exert its own proteolytic activity. In addition to the matrix destroying effect, certain of these MMPs such as MMP-3 have been implemented as the in vivo activator for other MMPs such as MMP-1 and MMP-9 (Ito, et al., *Arch Biochem. Biophys.* 267, 211, 1988; Ogata, et al., *J. Biol. Chem.*, 267, 3581, 1992). Thus, a cascade of proteolytic activity can be initiated by an excess of MMP-3. It follows that specific MMP-3 inhibitors should limit the activity of other MMPs that are not directly inhibited by such inhibitors.

It has also been reported that MMP-3 can cleave and thereby inactivate the endogenous inhibitors of other proteinases such as elastase (Winyard, et al., *FEBS Letts.* 279, 1, 91, 1991). Inhibitors of MMP-3 could thus influence the activity of other destructive proteinases by modifying the level of their endogenous inhibitors.

A number of diseases are thought to be mediated by excess or undesired matrix-destroying metalloprotease activity or by an imbalance in the ratio of the MMPs to the TIMPs. These include: a) osteoarthritis (Woessner, et al., *J. Biol. Chem.*, 259(6), 3633, 1984; Phadke, et al., *J. Rheumatol.* 10, 852, 1983), b) rheumatoid arthritis (Mullins, et al., *Biochim. Biophys. Acta* 695, 117, 1983; Woolley, et al., *Arthritis Rheum.* 20, 1231, 1977; Gravallese, et al., *Arthritis Rheum.* 34, 1076, 1991), c) septic arthritis (Williams, et al., *Arthritis Rheum.* 33, 533, 1990), d) tumor metastasis (Reich, et al., *Cancer Res.*, 48, 3307, 1988, and Matrisian, et al., *Proc. Nat'l. Acad. Sci., USA* 83, 9413, 1986), e) periodontal diseases (Overall, et al., *J. Periodontal Res.* 22, 81, 1987), f) corneal ulceration (Burns, et al., *Invest. Opthalmol. Vis. Sci.* 30, 1569, 1989), g) proteinuria (Baricos, et al., *Biochem. J.* 254, 609, 1988), h) coronary thrombosis from atherosclerotic plaque rupture (Henney, et al., *Proc. Nat'l. Acad. Sci., USA* 88, 8154–8158, 1991), I) aneurysmal aortic disease (Vine, et al., *Clin. Sci.* 81, 233, 1991), j) birth control (Woessner, et al., *Steroids* 54, 491, 1989), k) dystrophobic epidermolysis bullosa (Kronberger, et al., *J. Invest. Dermatol.* 79, 208, 1982), and l) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., *J. Neurochem.* 50, 688, 1988).

The need for new therapies is especially important in the case of arthritic diseases. The primary disabling effect of osteoarthritis (OA), rheumatoid arthritis (RA) and septic arthritis is the progressive loss of articular cartilage and thereby normal joint function. No marketed pharmaceutical agent is able to prevent or slow this cartilage loss, although nonsteroidal anti-inflammatory drugs (NSAIDs) have been given to control pain and swelling. The end result of these diseases is total loss of joint function which is only treatable by joint replacement surgery. MMP inhibitors are expected to halt or reverse the progression of cartilage loss and obviate or delay surgical intervention.

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9, respectively). For an overview of this field see Mullins, et al., *Biochim. Biophys. Acta* 695, 177, 1983; Ray, et al., *Eur. Respir. J.* 7, 2062, 1994; Birkedal-Hansen, et al., *Crit. Rev. Oral Biol. Med.* 4, 197, 1993.

Furthermore, it was demonstrated that inhibition of degradation of extracellular matrix by the native matrix metalloprotease inhibitor TIMP-2 (a protein) arrests cancer growth (DeClerck, et al., *Cancer Res.* 52, 701, 1992) and that TIMP-2 inhibits tumor-induced angiogenesis in experimental systems (Moses, et al. *Science* 248, 1408, 1990). For a review, see DeClerck, et al., *Ann. N.Y. Acad. Sci.* 732, 222, 1994. It was further demonstrated that the synthetic matrix metalloprotease inhibitor batimastat when given intraperitoneally inhibits human colon tumor growth and spread in an orthotopic model in nude mice (Wang, et al. *Cancer Res.* 54, 4726, 1994) and prolongs the survival of mice bearing human ovarian carcinoma xenografts (Davies, et. al., *Cancer Res.* 53, 2087, 1993). The use of this and related compounds has been described in Brown, et al., WO-9321942 A2 (931111).

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 A1; Beckett, et al., WO-9519956 A1; Beckett, et al., WO-9519957 A1; Beckett, et al., WO-9519961 A1; Brown, et al., WO-9321942 A2; Crimmin et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al,. EP 276436; and Myers, et al., EP 520573 A1. The preferred compounds of these patents have peptide backbones with a zinc complexing group (hydroxamic acid, thiol, carboxylic acid or phosphinic acid) at one end and a variety of sidechains, both those found in the natural amino acids as well as those with more novel functional groups. Such small peptides are often poorly absorbed, exhibiting low oral bioavailability. They are also subject to rapid proteolytic metabolism, thus having short half lives. As an example, batimastat, the compound described in Brown, et al., WO-9321942 A2, can only be given intra peritoneally.

Certain 3-biphenoylpropanoic and 4-biaryloylbutanoic acids are described in the literature as anti-inflammatory, anti-platelet aggregation, anti-phlogistic, anti-proliferative, hypolipidemic, antirheumatic, analgesic, and hypocholesterolemic agents. In none of these examples is a reference made to MMP inhibition as a mechanism for the claimed therapeutic effect. Certain related compounds are also used as intermediates in the preparation of liquid crystals.

Specifically, Tomcufcik, et al., U.S. Pat. No. 3,784,701 claims certain substituted benzoylpropionic acids to treat inflammation and pain. These compounds include 3-biphenoylpropanoic acid (a.k.a. fenbufen) shown below.

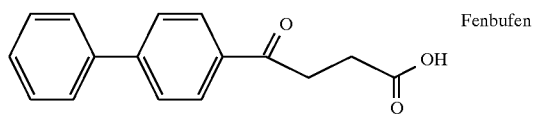

Fenbufen

Child, et al., *J. Pharm. Sci.*, 66, 466, 1977 describes structure-activity relationships of several analogs of fenbufen. These include several compounds in which the biphenyl ring system is substituted or the propanoic acid portion is substituted with phenyl, halogen, hydroxyl or methyl, or the carboxylic acid or carbonyl functions are converted to a variety of derivatives. No compounds are described which contain a 4'-substituted biphenyl and a substituted propanoic acid portion combined in one molecule. The phenyl (compounds XLIX and LXXVII) and methyl (compound XLVII) substituted compounds shown below were described as inactive.

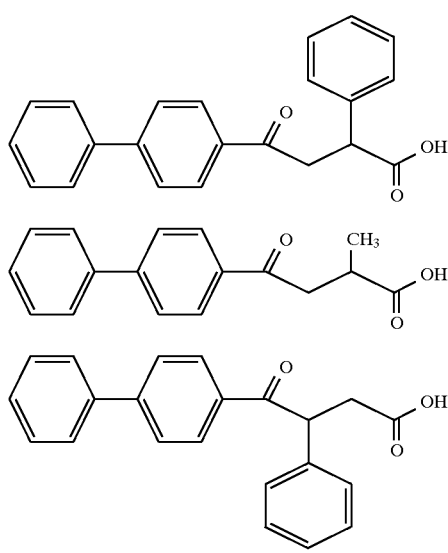

XLIX

XLVII

LXXVII

Kameo, et al., *Chem. Pharm. Bull.*, 36, 2050, 1988 and Tomizawa, et al., JP patent 62132825 A2 describe certain substituted 3-biphenoylpropionic acid derivatives and analogs thereof including the following. Various compounds with other substituents on the propionic acid portion are described, but they do not contain biphenyl residues.

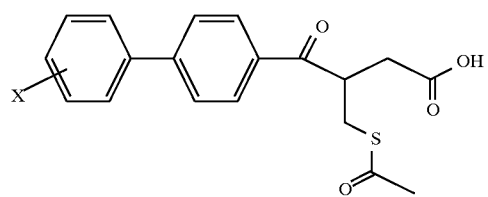

wherein X=H, 4'—Br, 4'—Cl, 4'—CH$_3$, or 2'—Br.

Cousse, et al., *Eur. J. Med. Chem.*, 22, 45, 1987 describe the following methyl and methylene substituted 3-biphenoyl-propanoic and -propenoic acids. The corresponding compounds in which the carbonyl is replaced with either CH$_2$OH or CH$_2$ are also described.

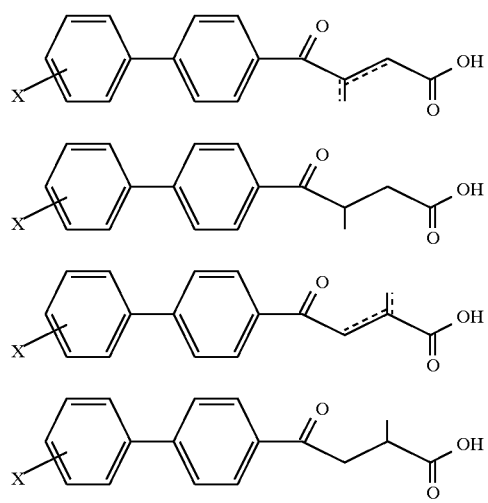

wherein X=H, Cl, Br, CH$_3$O, F, or NH$_2$.

Nichl, et at. DE patent 1957750 also describes certain of the above methylene substituted biphenoylpropanoic acids.

El-Hashash, et al., *Revue Roum. Chim.* 23, 1581, 1978 describe products derived from β-aroyl-acrylic acid epoxides including the following biphenyl compound. No compounds substituted on the biphenyl portion are described.

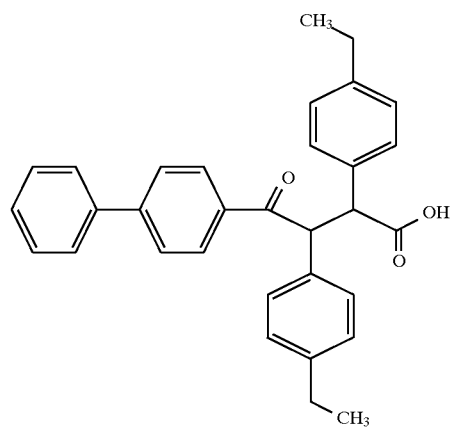

Kitamura, et al., JP patent 60209539 describes certain biphenyl compounds used as intermediates for the production of liquid crystals including the following. The biphenyl is not substituted in these intermediates.

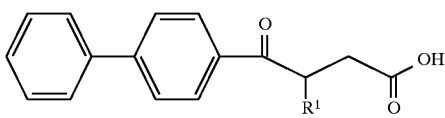

wherein $R^1$ is an alkyl of 1–10 carbons.

Thyes, et al., DE patent 2854475 uses the following compound as an intermediate. The biphenyl group is not substituted.

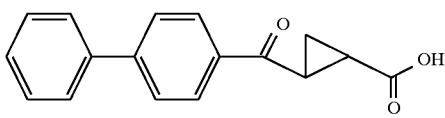

Sammour, et al., *Egypt J. Chem.* 15, 311, 1972 and Couquelet, et al., *Bull. Soc. Chim. Fr.* 9, 3196, 1971 describe certain dialkylamino substituted biphenoylpropanoic acids including the following. In no case is the biphenyl group substituted.

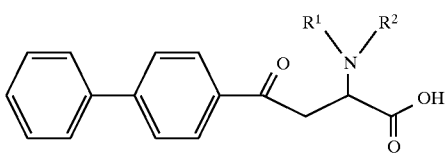

wherein $R^1$, $R^2$=alkyl, benzyl, H, or, together with the nitrogen, morpholinyl.

Others have disclosed a series of biphenyl-containing carboxylic acids, illustrated by the compound shown below, which inhibit neural endopeptidase (NEP 24.11), a membrane-bound zinc metalloprotease (Stanton, et al., *Bioorg. Med. Chem. Lett.* 4, 539, 1994; Lombaert, et al., *Bioorg. Med. Chem. Lett.* 4, 2715, 1994; Lombaert, et al., *Bioorg. Med. Chem. Lett.* 5, 145, 1995; Lombaert, et al., *Bioorg. Med. Chem. Lett.* 5, 151, 1995).

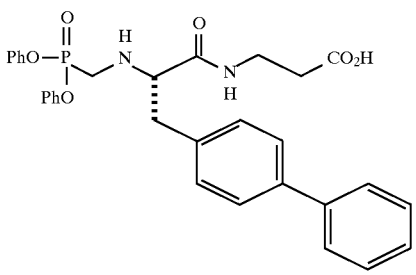

It has been reported that N-carboxyalkyl derivatives containing a biphenylethylglycine, illustrated by the compound shown below, are inhibitors of stromelysin-1 (MMP-3), 72 kDA gelatinase (MMP-2) and collagenase (Durette, et al., WO-9529689).

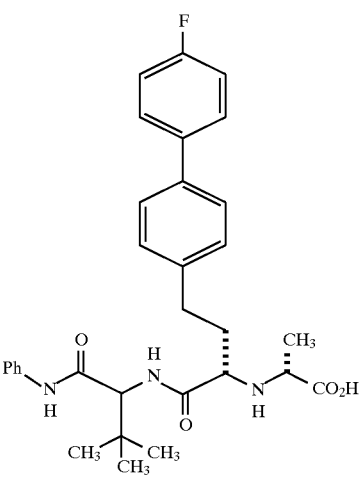

It would be desirable to have effective MMP inhibitors which possess improved bioavailability and biological stability relative to the peptide-based compounds of the prior art, and which can be optimized for use against particular target MMPs. Such compounds are the subject of the present application.

The development of efficacious MMP inhibitors would afford new therapies for diseases mediated by the presence of, or an excess of MMP activity, including osteoarthritis, rheumatoid arthritis, septic arthritis, tumor metastasis, periodontal diseases, corneal ulcerations, and proteinuria. Several inhibitors of MMPs have been described in the literature, including thiols (Beszant, et al., *J. Med. Chem.* 36, 4030, 1993), hydroxamic acids (Wahl, et al. *Bioorg. Med. Chem. Lett.* 5, 349, 1995; Conway, et al. *J. Exp. Med.* 182, 449, 1995; Porter, et al., *Bioorg. Med. Chem. Lett.* 4, 2741, 1994; Tomczuk, et al., *Bioorg. Med. Chem. Lett.* 5, 343, 1995; Castelhano, et al., *Bioorg. Med. Chem. Lett.* 5, 1415, 1995), phosphorous-based acids (Bird, et al. *J. Med. Chem.* 37, 158, 1994; Morphy, et al., *Bioorg. Med. Chem. Lett.* 4, 2747, 1994; Kortylewicz, et al., *J. Med. Chem.* 33, 263, 1990), and carboxylic acids (Chapman, et al. *J. Med. Chem.* 36, 4293, 1993; Brown, et al. *J. Med. Chem.* 37, 674, 1994; Morphy, et al., *Bioorg. Med. Chem. Lett.* 4, 2747, 1994; Stack, et al., *Arch. Biochem. Biophys.* 287, 240, 1991; Ye, et al., *J. Med. Chem.* 37, 206, 1994; Grobelny, et al., *Biochemistry* 24, 6145, 1985; Mookhtiar, et al., *Biochemistry* 27, 4299, 1988). However, these inhibitors generally contain peptidic backbones, and thus usually exhibit low oral bioactivity due to poor absorption and short half lives due to rapid proteolysis. Therefore, there remains a need for improved MMP inhibitors.

SUMMARY OF THE INVENTION

This invention provides compounds having matrix metalloprotease inhibitory activity. These compounds are useful for inhibiting matrix metalloproteases and, therefore, combating conditions to which MMP's contribute. Accordingly, the present invention also provides pharmaceutical compositions and methods for treating such conditions. The compounds described relate to a method of treating a human to achieve an effect, in which the effect is: alleviation of osteoarthritis, rheumatoid arthritis, septic arthritis, periodontal disease, corneal ulceration, proteinuria, aneurysmortic disease, dystrophic epidermolysis bullosa, conditions leading to inflammatory responses, osteopenias mediated by MMP activity, tempero mandibular joint disease, or demyelinating diseases of the nervous system; tumor metastasis and degenerative cartilage loss following traumatic joint injury; and reduction of coronary thrombosis from atherosclerotic plaque rupture. The compounds of the invention are also useful for birth control. The method according to the invention comprises administering an amount of a compound or composition of the invention as described above, and in more detail in the detailed description below, which is effective to inhibit the activity of at least one matrix metalloprotease, resulting in achievement of the desired effect. The compounds of the present invention are also useful scientific research tools for studying functions and mechanisms of action of matrix metalloproteases in both in vivo and in vitro systems. Because of their MMP-inhibiting activity, the present compounds can be used to modulate MMP action, thereby allowing the researcher to observe the effects of reduced MMP activity in the experimental biological system under study.

This invention relates to compounds having matrix metalloprotease inhibitory activity and the generalized formula:

$(T)_x$-A-B-D-E-G  (L)

In the above generalized formula (L), $(T)_x$A represents a substituted or unsubstituted aromatic 6-membered ring or heteroaromatic 5–6 membered ring containing 1–2 atoms of N, O, or S. T represents one or more substituent groups, the subscript x represents the number of such substituent groups, and A represents the aromatic or heteroaromatic ring, designated as the A ring or A unit. When N is employed in conjunction with either S or O in the A ring, these heteroatoms are separated by at least one carbon atom.

The substituent group(s) T are independently selected from the group consisting of halogen; alkyl; haloalkyl; alkenyl; alkynyl, benzyloxy, alkyloxy; $-(CH_2)_pQ$ in which p is 0 or an integer of 1–4; and -alkenyl-Q in which the alkenyl moiety comprises 2–4 carbons. Q in the latter two groups is selected from the group consisting of aryl, heteroaryl, $-CN$, $-CHO$, $-NO_2$, $-CO_2R^2$, $-OCOR^2$, $-SOR^3$, $-SO_2R^3$, $-CON(R^2)_2$, $-SO_2N(R^2)_2$, $-COR^2$, $-N(R^2)_2$, $-N(R_2)COR^2$, $-N(R^2)CO_2R^3$, $-N(R^2)CON(R^2)_2$, $-CHN_4$, $-OR^4$, and $-SR^4$. In these formulae $R^2$ represents H, alkyl, aryl, heteroaryl, arylalkyl, or heteroarylalkyl; $R^3$ represents alkyl, aryl, heteroaryl, arylalkyl, or heteroaryl-alkyl; and $R^4$ represents H, alkyl, aryl, heteroaryl, arylalkyl, heteroaryl-alkyl, alkenyl, alkynyl, haloalkyl, acyl, or alkyleneoxy or polyalkyleneoxy terminated with H, alkyl, or phenyl. Unsaturation in a moiety which is attached to Q or which is part of Q is separated from any N, O, or S of Q by at least one carbon atom. The A ring may be unsubstituted or may carry up to 2 substituents T. Accordingly, the subscript x is 0, 1, or 2.

In the generalized formula (L), B represents an aromatic 6-membered ring or a heteroaromatic 5–6 membered ring containing 1–2 atoms of N, O, or S. It is referred to as the B ring or B unit. When N is employed in conjunction with either S or O in the B ring, these heteroatoms are separated by at least one carbon atom.

In the generalized formula (L), D represents

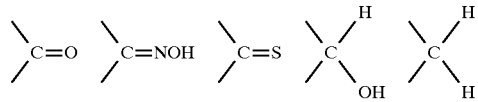

In the generalized formula (L), E represents a moiety of the formula

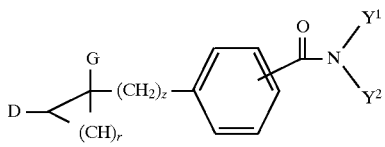

where r is 0–2, z is 1–4, $Y^1$ is H or $CH_3$, and $Y^2$ is an alkyl of 3–6 carbons, a primary or secondary aminoalkyl of 3–6 carbons, a carboxylic acid of 2–5 carbons, a (1-morpholinyl) alkyl wherein the alkyl group is 0–5 carbons, an ester of 3–5 carbons, a ketone of 3–5 carbons, or a arylalkyl wherein the alkyl group is 3–5 carbons; or $Y^1$ and $Y^2$ together with the nitrogen atom to which they are attached form a 1-piperidinyl or 1-morpholinyl ring. D and G as used in the above structure represent the D and G units of the general formula (L) and are not part of the E unit; they are included merely to indicate how the D, E and G groups are linked. When r=0 the structure above takes the form:

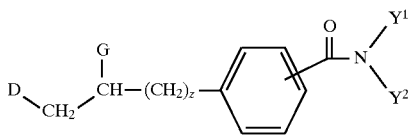

When r=2 the alkyl moiety includes a cyclobutyl ring and when r=3 the alkyl moiety includes a cyclopentyl ring.

In the generalized formula (L), G represents $-PO_3H_2$, —M

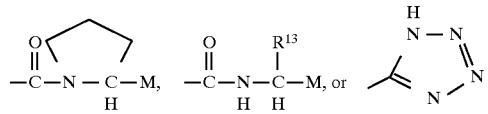

in which M represents $-CO_2H$, $-CON(R^{11})_2$, or $-CO_2R^{12}$, $R^{12}$ represents alkyl of 1–4 carbons, and $R^{13}$ represents any of the side chains of the 19 noncyclic naturally occurring amino acids.

Pharmaceutically acceptable salts of these compounds are also within the scope of the invention.

In most related reference compounds of the prior art, the biphenyl portion of the molecule is unsubstituted, and the propanoic or butanoic acid portion is either unsubstituted or has a single methyl or phenyl group. Presence of the larger phenyl group has been reported to cause prior art compounds to be inactive as anti-inflammatory analgesic agents. See, for example, Child, et al., *J. Pharm. Sci.* 66, 466, 1977. By contrast, it has now been found that compounds which exhibit potent MMP inhibitory activity contain a substituent of significant size on the propanoic or butanoic portion of the molecule. The biphenyl portions of the best MMP inhibitors also preferably contain a substituent on the 4'-position, although when the propanoic or butanoic portions are optimally substituted, the unsubstituted biphenyl compounds of the invention have sufficient activity to be considered realistic drug candidates.

The foregoing merely summarizes certain aspects of the present invention and is not intended, nor should it be construed, to limit the invention in any way. All of the patents and other publications recited in this specification are hereby incorporated by reference in their entirety.

DESCRIPTION OF THE PREFERRED EMBODIMENTS

This invention provides compounds having matrix metalloprotease inhibitory activity. These compounds are useful for inhibiting matrix metalloproteases and, therefore, combating conditions to which MMP's contribute. Accordingly, the present invention also provides pharmaceutical compositions and methods for treating such conditions. The compounds described relate to a method of treating a human to achieve an effect, in which the effect is: alleviation of osteoarthritis, rheumatoid arthritis, septic arthritis, periodontal disease, corneal ulceration, proteinuria, aneurysmortic disease, dystrophic epidermolysis bullosa, conditions leading to inflammatory responses, osteopenias mediated by MMP activity, tempero mandibular joint disease, or demyelinating diseases of the nervous system; tumor metastasis and degenerative cartilage loss following traumatic joint injury; and reduction of coronary thrombosis from atherosclerotic plaque rupture. The compounds of the invention are also useful for birth control. The method according to the invention comprises administering an amount of a compound or composition of the invention as described above, and in more detail in the detailed description below, which is effective to inhibit the activity of at least one matrix metalloprotease, resulting in achievement of the desired effect. The compounds of the present invention are also useful scientific research tools for studying functions and mechanisms of action of matrix metalloproteases in both in vivo and in vitro systems. Because of their MMP-inhibiting activity, the present compounds can be used to modulate MMP action, thereby allowing the researcher to observe the effects of reduced MMP activity in the experimental biological system under study.

More particularly, the compounds of the present invention are materials having matrix metalloprotease inhibitory activity and the generalized formula:

$$(T)_x\text{-A-B-D-E-G} \quad (L)$$

in which $(T)_x$A represents a substituted or unsubstituted aromatic or heteroaromatic moiety selected from the group consisting of:

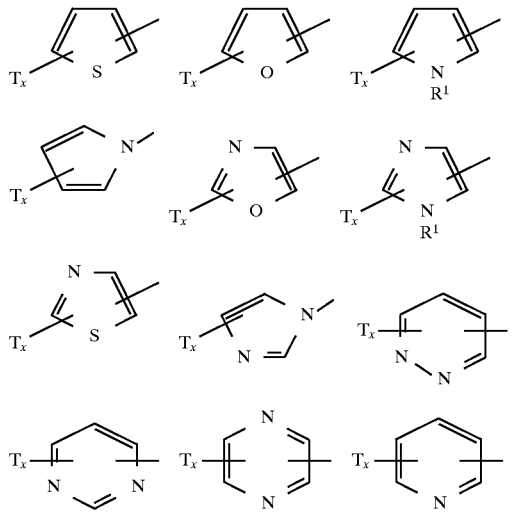

in which $R^1$ represents H or alkyl of 1–3 carbons.

Throughout this application, in the displayed chemical structures, an open bond indicates the point at which the structure joins to another group. For example,

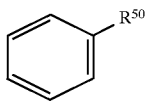

where $R^{50}$ is

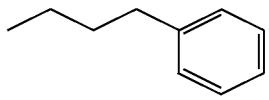

is the structure

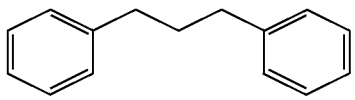

In these structures, the aromatic ring is referred to as the A ring or A unit, and each T represents a substituent group, referred to as a T group or T unit. Substituent groups T are independently selected from the group consisting of: the halogens —F, —Cl, —Br, and —I; alkyl of 1–10 carbons; haloalkyl of 1–10 carbons; alkenyl of 2–10 carbons; alkynyl of 2–10 carbons; benzyloxy, alkyloxy of 1–5 carbons; —(CH$_2$)$_p$Q in which p is 0 or an integer 1–4, and -alkenyl-Q in which the alkenyl moiety comprises 2–4 carbons. Q in each of the latter two groups is selected from the group consisting of aryl of 6–10 carbons; heteroaryl comprising 4–9 carbons and at least one N, O, or S heteroatom, —CN, —CHO, —NO$_2$, —CO$_2$R$^2$, —OCOR$^2$, —SOR$^3$, —SO$_2$R$^3$, —CON(R$^2$)$_2$, —SO$_2$N(R$^2$)$_2$, —C(O)R$^2$, —N(R$^2$)$_2$, —N(R$^2$)COR$^2$, N(R$^2$)CO$_2$R$^3$, —N(R$^2$)CON(R$^2$)$_2$, —CHN$_4$, —OR$^4$, and SR$^4$. The groups R$^2$, R$^3$, and R$^4$ are defined as follows.

R$^2$ represents H; alkyl of 1–6 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

R$^3$ represents alkyl of 1–4 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

R$^4$ represents H; alkyl of 1–12 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; heteroaryl-alkyl in which the heteroaryl portion comprises 4–9 carbons and at least one N, O, or S heteroatom and the alkyl portion contains 1–4 carbons; alkenyl of 2–12 carbons; alkynyl of 2–12 carbons; —(C$_q$H$_{2q}$O)$_r$R$^5$ in which q is 1–3, r is 1–3, and R$^5$ is H provided q is greater than 1, or R$^5$ is alkyl of 1–4 carbons, or phenyl; —(CH$_2$)$_3$X in which s is 2–3 and X is halogen; or —C(O)R$^2$.

Any unsaturation in a moiety which is attached to Q or which is part of Q is separated from any N, O, or S of Q by at least one carbon atom, and the number of substituents, designated x, is 0, 1, or 2.

The substituent group T can also be an acetylene containing moiety with the general formula:

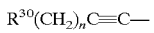

where n is 1–4 and $R^{30}$ is selected from the group consisting of: HO—, MeO—, (n—Pr)$_2$N—, CH$_3$CO$_2$—, CH$_3$CO$_2$OCO$_2$—, HO$_2$C—, HOC—, Ph—, 3—OH—Ph—, and PhCH$_2$O—, provided that when $R^{30}$ is Ph or 3—OH—Ph, n=0.

The B ring of generalized formula (L) is a substituted or unsubstituted aromatic or heteroaromatic ring, in which any substituents are groups which do not cause the molecule to fail to fit the active site of the target enzyme, or disrupt the relative conformations of the A and B rings, such that they would be detrimental. Such groups may be moieties such as lower alkyl, lower alkoxy, CN, NO$_2$, halogen, etc., but are not to be limited to such groups. In the generalized formula (L), B represents an aromatic or heteroaromatic ring selected from the group consisting of:

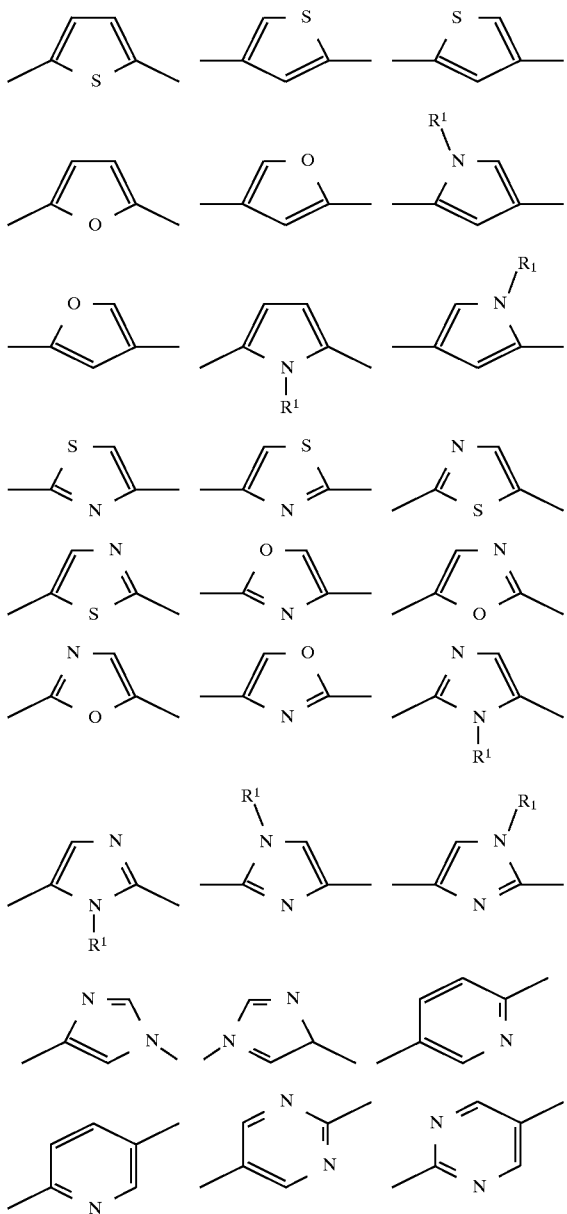

-continued

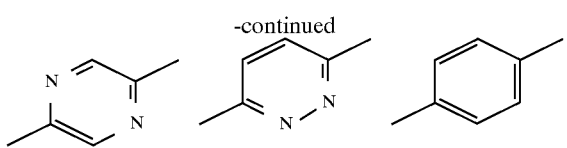

in which $R^1$ is defined as above. These rings are referred to as the B ring or B unit.

Compounds of the general formula (L) include those in which the combination of (T)$_x$-A-B, rather than taking one of the forms described above, has the structure:

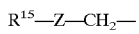

where Z may be (CH$_2$)$_e$—C$_6$H$_4$—(CH$_2$)$_f$ or (CH$_2$)$_g$, e=0–8, f=0–5 and g=0–10. $R^{15}$ may be a straight, or cyclic alkyl group of 6–12 carbons atoms, preferably of 7–11 carbon atoms, and optionally may bear one or more pharmaceutically acceptable substituents which are discussed more fully below. Any branching or substitution is preferably located at least three chain atoms away from the point of attachment of the $R^{15}$ group to the phenyl ring.

$R^{15}$ may also be a polyether of the formula $R^{32}$O(C$_2$H$_4$O)$_h$, in which the subscript "h" is 1 or 2, and the group $R^{32}$ is a straight, branched or cyclic alkyl group of 1–5 carbon atoms, preferably of 1–3 carbon atoms and straight, or phenyl, or benzyl. $R^{32}$ optionally may bear one or more pharmaceutically-acceptable substituents which are discussed more fully below. Any branching or substitution is preferably located at least three chain atoms away from the point of attachment of the polyether $R^{15}$ group to the phenyl ring.

$R^{15}$ may also be a substituted alkynyl group of the formula:

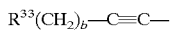

in which the subscript "b" is 1–10 and the group $R^{33}$ is H—, HO— or $R^{34}$O— and the group is preferably the HO— group. $R^{34}$ may be an alkyl group of 1–3 carbon atoms, or phenyl or benzyl. $R^{33}$ optionally may bear one or more pharmaceutically-acceptable substituents which are discussed more fully below.

$R^{15}$ may also be —H, —Cl, —OMe or

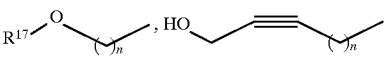

wherein n is 0–4, and $R^{17}$ is C$_2$H$_5$, allyl or benzyl.

In the generalized formula (L), D represents the moieties:

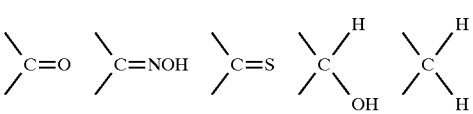

In the generalized formula (L), E represents a moiety of the formula

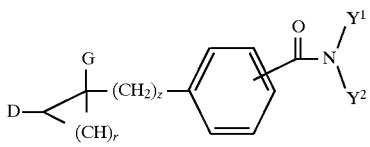

where r is 0–2, z is 1–4, $Y^1$ is H or $CH_3$, and $Y^2$ is an alkyl of 3–6 carbons, a primary or secondary aminoalkyl of 3–6 carbons, a carboxylic acid of 2–5 carbons, a (1-morpholinyl) alkyl wherein the alkyl group is 0–5 carbons, an ester of 3–5 carbons, a ketone of 3–5 carbons, or a arylalkyl wherein the alkyl group is 3–5 carbons; or $Y^1$ and $Y^2$ together with the nitrogen atom to which they are attached form a 1-piperidinyl or 1-morpholinyl ring. D and G as used in the above structure represent the D and G units of the general formula (L) and are not part of the E unit; they are included merely to indicate how the D, E and G groups are linked. When r=0 the structure above takes the form:

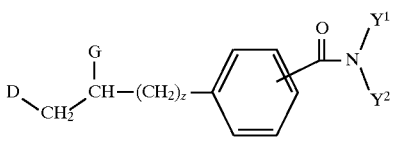

When r=2 the alkyl moiety includes a cyclobutyl ring and when r=3 the alkyl moiety includes a cyclopentyl ring.

In addition, aryl or heteroaryl portions of any of the T groups optionally may bear up to two substituents selected from the group consisting of —$(CH_2)_yC(R^{11})(R^{12})OH$, —$(CH_2)_yOR^{11}$, —$(CH_2)_ySR^{11}$, —$(CH_2)_yS(O)R^{11}$, —$(CH_2)_yS(O)_2R^{11}$, —$(CH_2)_ySO_2N(R^{11})_2$, —$(CH_2)_yN(R^{11})_2$, —$(CH_2)_yN(R^{11})COR^{12}$, —$OC(R^{11})_2O$— in which both oxygen atoms are connected to the aryl ring, —$(CH)_2C_yOR^{11}$, —$(CH_2)_yCON(R^{11})_2$, —$(CH_2)_yCO_2R^{11}$, —$(CH_2)_yOCOR^{11}$-halogen, —CHO, —$CF_3$, —$NO_2$, —CN, and —$R^{12}$, in which y is 0–4; $R^{11}$ represents H or alkyl of 1–4 carbons; and $R^{12}$ represents alkyl of 1–4 carbons.

In the generalized formula (L), G represents —$PO_3H_2$ —M

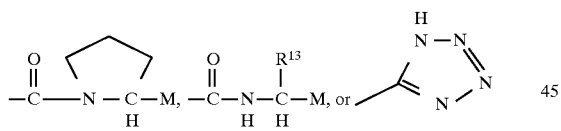

in which M represents —$CO_2H$, —$CON(R^{11})_2$, or —$CO_2R^{12}$, and $R^{13}$ represents any of the side chains of the 19 noncyclic naturally occurring amino acids. Pharmaceutically acceptable salts of the compounds falling within the generalized formula (L) are also within the invention.

In the compounds of the invention, the following are preferred.

The substituent group T is preferably halogen (most preferably Cl),

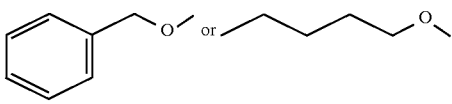

The subscript x, which defines the number of T substituents, is preferably 1 or 2, most preferably 1, and this substituent is on the 4-position of ring A.

The A ring is preferably a phenyl or thiophene ring, most preferably phenyl.

The B ring is preferably a 1,4-phenylene or 2,5-thiophene ring, most preferably 1,4-phenylene.

The D unit is most preferably a carbonyl group.

The E unit is preferably:

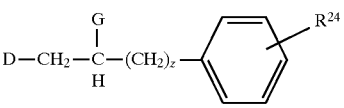

where, as before, D and G are the D and G units and are not part of E, z is 1–4 (most preferably 2) and $R^{24}$ is one of the following

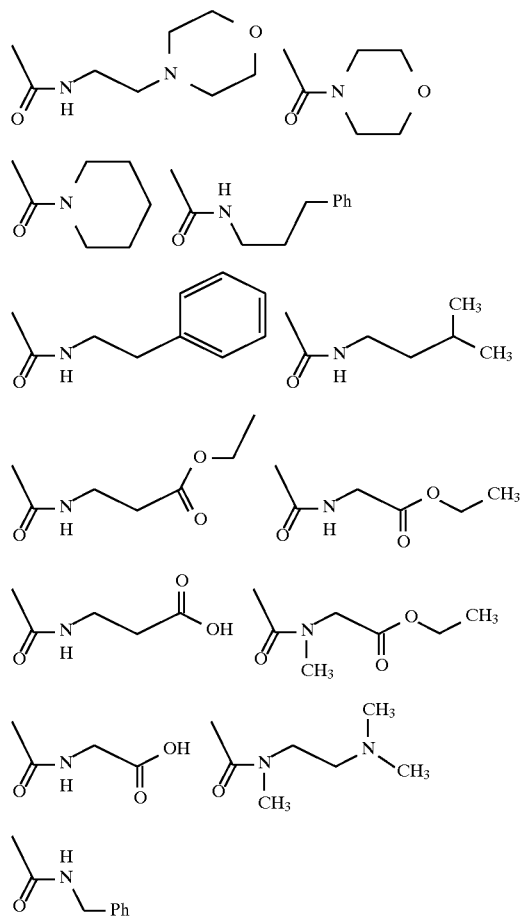

The G unit is most preferably a carboxylic acid group.

It is to be understood that as used herein, the term "alkyl" means straight, branched, cyclic, and polycyclic materials. The term "haloalkyl" means partially or fully halogenated alkyl groups such as —$(CH_2)_2Cl$, —$CF_3$ and —$C_6F_{13}$, for example.

In one of its embodiments, the invention relates to compounds of generalized formula (L) in which at least one of the units A, B, T, and E comprises a heteroaromatic ring. Preferred heteroaromatic ring-containing compounds are those in which the heteroaryl groups are heteroaryl of 4–9 carbons comprising a 5–6 membered heteroaromatic ring containing O, S, or $NR^1$ when the ring is 5-membered, and N when said ring is 6-membered. Particularly preferred heteroaromatic ring-containing compounds are those in which at least one of the A and B units comprises a thiophene ring. When the A unit is thiophene, it is preferably connected to B unit at position 2 and carries one substituent group T on position 5. When B Unit is thiophene, it is preferably connected through positions 2 and 5 to D and A units respectively.

In the generalized formula (L), the A and B rings are preferably phenyl and phenylene, respectively, the A ring preferably bears at least one substituent group T preferably located on the position furthest from the position of the A ring which is connected to the B ring, the D unit is preferably a carbonyl group, and the G unit is preferably a carboxyl group.

In a particularly preferred embodiment, the compounds of the invention have the formula:

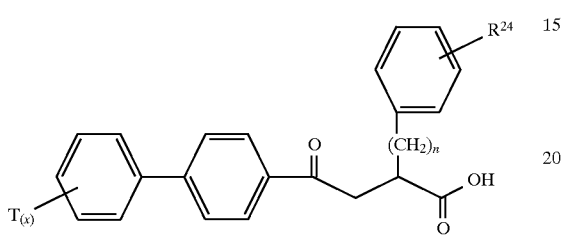

in which x is 1 or 2, one substituent group T is located on the 4-position of the A ring, relative to the point of attachment between the A and B rings, n=1–5 and $R^{24}$ is ortho, meta or para to the $(CH_2)_n$ and is selected from one of the following:

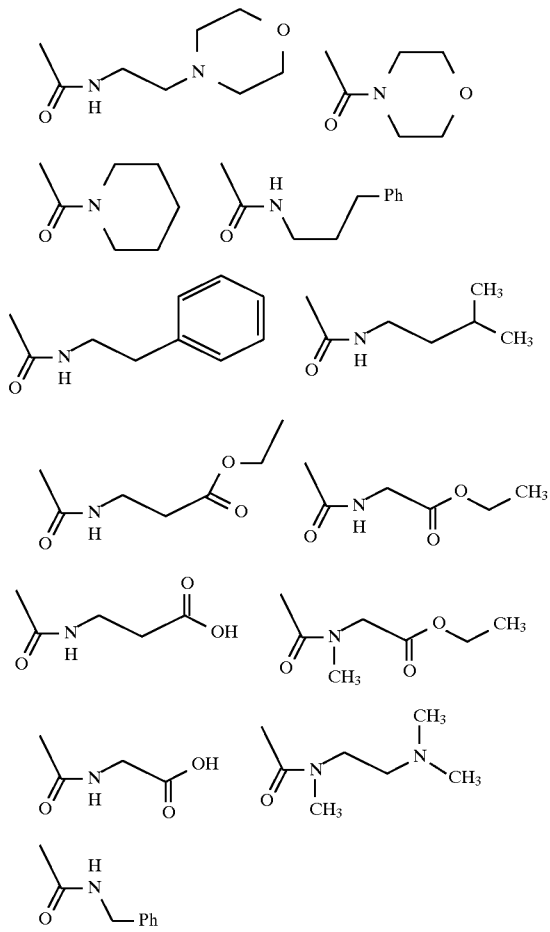

Substituent group T of this subset is preferably a halogen,

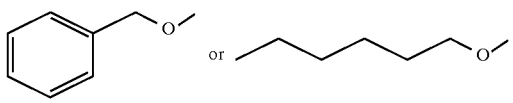

T is most preferably Cl and is in the para position of the A ring relative to the B ring.

The invention also relates to certain intermediates useful in the synthesis of some of the claimed inhibitors. These intermediates are compounds having the generalized formula:

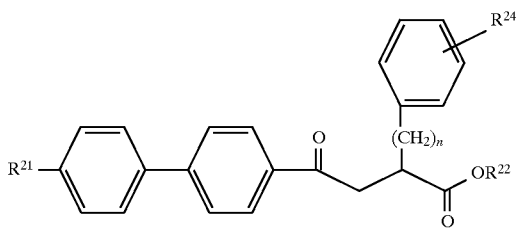

where n=1–5, $R^{21}$ is a halogen and $R^{22}$ is H or an alkyl (preferably ethyl) or allylalkyl (wherein the alkyl is preferably methyl) group.

Those skilled in the art will appreciate that many of the compounds of the invention exist in enantiomeric or diastereomeric forms, and that it is understood by the art that such stereoisomers generally exhibit different activities in biological systems. This invention encompasses all possible stereoisomers which possess inhibitory activity against an MMP, regardless of their stereoisomeric designations, as well as mixtures of stereoisomers in which at least one member possesses inhibitory activity.

The most prefered compounds of the present invention are as indicated and named in the list below:

I) 4'-chloro-γ-oxo-α-[2-[2-[[(2-phenylethyl)amino] carbonyl]phenyl]ethyl]-[1,1'-biphenyl]-4-butanoic acid, II) 4'-chloro-α-[2-[2-[[(4-morpholinylcarbonyl)phenyl] ethyl]-γ-oxo-[1,1'-biphenyl]-4-butanoic acid, III) 4'-chloro-γ-oxo-α-[2-[2-[[(phenylmethyl)amino] carbonyl]phenyl]ethyl]-[1,1'-biphenyl]-4-butanoic acid, IV) 4'-chloro-γ-oxo-α-[2-[2-[[(3-phenylpropyl)amino] carbonyl]phenyl]ethyl]-[1,1'-biphenyl]-4-butanoic acid, V) 4'-chloro-γ-oxo-α-[2-[2-(1-piperidinylcarbonyl) phenyl]ethyl]-[1,1'-biphenyl]-4-butanoic acid, VI) 4'-chloro-α-[2-[2-[[(3-methylbutyl)amino]carbonyl] phenyl]ethyl]-γ-oxo-[1,1'-biphenyl]-4-butanoic acid, VII) 4'-chloro-α-[2-[2-[[(3-ethoxybutyl)amino]carbonyl] phenyl]ethyl]-γ-oxo-[1,1'-biphenyl]-4-butanoic acid, VIII) 4'-chloro-α-[2-[2-[[(2-ethoxyethyl)amino]carbonyl] phenyl]ethyl]-γ-oxo-[1,1'-biphenyl]-4-butanoic acid, IX) 4'-chloro-α-[2-[2-[[(2-ethoxy-2-oxoethyl) methylamino]carbonyl]phenyl]ethyl]-γ-oxo-[1,1'-biphenyl]-4-butanoic acid, X) 4'-chloro-α-[2-[3-(4-morpholinylcarbonyl)phenyl] ethyl]-γ-oxo-[1,1'-biphenyl]-4-butanoic acid, XI) 4'-chloro-γ-oxo-α-[2-[3-(1-piperidinylcarbonyl) phenyl]ethyl]-[1,1'-biphenyl]-4-butanoic acid, XII) 4'-chloro-γ-oxo-α-[2-[3-[[(2-phenylethyl)amino] carbonyl]phenyl]ethyl]-[1,1'-biphenyl]-4-butanoic acid, XIII) 4'-chloro-γ-oxo-α-[2-[3-[[(3-phenylpropyl)amino] carbonyl]phenyl]ethyl]-[1,1'-biphenyl]-4-butanoic acid, XIV) 4'-chloro-α-[2-[3-[[(3-methylbutyl)amino] carbonyl]phenyl]ethyl]-γ-oxo-[1,1'-biphenyl]-4-butanoic acid, XV) 4'-chloro-γ-oxo-α-[2-[3-[[(phenylmethyl)amino]carbonyl]phenyl]ethyl]-[1,1'-biphenyl]-4-butanoic acid, XVI) 4'-chloro-α-[2-[3-[[(2-ethoxy-2-oxoethyl)methylamino]carbonyl]phenyl]ethyl]-γ-oxo-[1,1'-biphenyl]-4-butanoic acid, XVII) 4'-chloro-α-[2-[4-(4-morpholinylcarbonyl)phenyl]ethyl]-γ-oxo-[1,1'-biphenyl]-4-butanoic acid, XVIII) 4'-chloro-α-[2-[4-[[(3-methylbutyl)amino]carbonyl]phenyl]ethyl]-γ-oxo-[1,1'-biphenyl]-4-butanoic acid, XIX) 4'-chloro-α-[2-[4-[[(2-ethoxy-2-oxoethyl)amino]carbonyl]phenyl]ethyl]-γ-oxo-[1,1'-biphenyl]-4-butanoic acid, XX) 4'-chloro-γ-oxo-α-[2-[4-[[(2-phenylethyl)amino]carbonyl]phenyl]ethyl]-[1,1'-biphenyl]-4-butanoic acid, XXI) 4'-chloro-γ-oxo-α-[2-[4-(1-piperidinylcarbonyl)phenyl]ethyl]-[1,1'-Biphenyl]-4-butanoic acid iphenyl]-4-butanoic acid, XXII) 4'-chloro-γ-oxo-α-[2-[2-[[(2-phenylethyl)amino]carbonyl]phenyl]ethyl]-[1,1'-biphenyl-4-butanoic acid, XXIII) α-[2-[2-[[(2-carboxyethyl)amino]carbonyl]phenyl]ethyl]-4'-chloro-γ-oxo-[1,1'-biphenyl]-4-butanoic acid, XIV) α-[2-[4[[(carboxymethyl)amino]carbonyl]phenyl]ethyl]-4'-chloro-γ-oxo-(1,1'-biphenyl]-4-butanoic acid, XXV) 4'-chloro-α-[2 [2-[[[2-(4-morpholinyl)ethyl]amino]carbonyl]phenyl]ethyl]-γ-oxo-[1,1'-biphenyl]-4-butanoic acid, XVI) α-[2-[3-[[(2-carboxyethyl)amino]carbonyl]phenyl]ethyl]-4'-chloro-γ-oxo-[1,1'-biphenyl]-4-butanoic acid, XXVII) 4'-chloro-α-[2-[3-[[[2-(-morpholinyl)ethyl]amino]carbonyl]phenyl]ethyl]-γ-oxo-[1,1'-biphenyl]-4-butanoic acid, XXVIII) 4'-chloro-α-[2-4-[[[2-(4-morpholimyl)ethyl]amino]carbonyl]phenyl]ethyl]-γ-oxo-[1,1'-biphenyl]-4-butanoic acid, XXIX) 4'-chloro-α-[2-[3-[[[2-dimethylamino)-2-oxoethyl]methylamino]carbonyl]-phenyl]ethyl]-γ-oxo-[1,1'biphenyl]-4-butanoic acid, XXX) γ-oxo-4'-(phenylmethoxy)-α-[2-3-(1-piperidinylcarbonyl)phenyl]ethyl]-[1,1'-biphenyl]-4-butanoic acid, XXXI) γ-oxo-4'-(pentyloxy)-α-[2-[3-(1-piperidinylcarbonyl)phenyl]ethyl]-[1,1'-biphenyl]-4-butanoic acid, and XXXII) γ-oxo-α-[2-[2-[(2-oxo-1-piperidinyl)methyl]phenyl]ethyl]-4'-(phenylmethoxy)-[1,1'-biphenyl]-4-butanoic acid.

General Preparative Methods:

The compounds of the invention may be prepared by use of known chemical reactions and procedures. Nevertheless, the following general preparative methods are presented to aid the reader in synthesizing the inhibitors, with more detailed particular examples being presented below in the experimental section describing the working examples.

Suitable pharmaceutically acceptable salts of the compounds of the present invention include addition salts formed with organic or inorganic bases. The salt forming ion derived from such bases can be metal ions, e.g., aluminum, alkali metal ions, such as sodium or potassium, alkaline earth metal ions such as calcium or magnesium, or an amine salt ion, of which a number are known for this purpose. Examples include ammonium salts, arylalkylamines such as dibenzylamine and N,N-dibenzylethylenediamine, lower alkylamines such as methylamine, t-butylamine, procaine, lower alkylpiperidines such as N-ethylpiperidine, cycloalkylamines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described below and are preferred.

These and other salts which are not necessarily physiologically acceptable are useful in isolating or purifying a product acceptable for the purposes described below. For example, the use of commercially available enantiomerically pure amines such as (+)-cinchonine in suitable solvents can yield salt crystals of a single enatiomer of the invention compounds, leaving the opposite enantiomer in solution in a process often referred to as "classical resolution." As one enantiomer of a given invention compound is usually substantially greater in physiological effect than its antipode, this active isomer can thus be found purified in either the crystals or the liquid phase. The salts are produced by reacting the acid form of the invention compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compounds of the present invention have been found to inhibit the matrix metalloproteases MMP-3, MMP-9 and MMP-2, and to a lesser extent MMP-1, and are therefore useful for treating or preventing the conditions referred to in the background section. As other MMPs not listed above share a high degree of homology with those listed above, especially in the catalytic site, it is deemed that compounds of the invention should also inhibit such other MMPs to varying degrees. Varying the substituents on the biaryl portions of the molecules, as well as those of the propanoic or butanoic acid chains of the claimed compounds, has been demonstrated to affect the relative inhibition of the listed MMPs. Thus compounds of this general class can be "tuned" by selecting specific substituents such that inhibition of specific MMP(s) associated with specific pathological conditions can be enhanced while leaving non-involved MMPs less affected.

The method of treating matrix metalloprotease-mediated conditions may be practiced in mammals, including humans, which exhibit such conditions.

The inhibitors of the present invention are contemplated for use in veterinary and human applications. For such purposes, they will be employed in pharmaceutical compositions containing active ingredient(s) plus one or more pharmaceutically acceptable carriers, diluents, fillers, binders, and other excipients, depending on the administration mode and dosage form contemplated.

Administration of the inhibitors may be by any suitable mode known to those skilled in the art. Examples of suitable parenteral administration include intravenous, intraarticular, subcutaneous and intramuscular routes. Intravenous administration can be used to obtain acute regulation of peak plasma concentrations of the drug. Improved half-life and targeting of the drug to the joint cavities may be aided by entrapment of the drug in liposomes. It may be possible to improve the selectivity of liposomal targeting to the joint cavities by incorporation of ligands into the outside of the liposomes that bind to synovial-specific macromolecules. Alternatively intramuscular, intraarticular or subcutaneous depot injection with or without encapsulation of the drug into degradable microspheres e.g., comprising poly(DL-lactide-co-glycolide) may be used to obtain prolonged sustained drug release. For improved convenience of the dosage form it may be possible to use an i.p. implanted reservoir and septum such as the Percuseal system available from Pharmacia. Improved convenience and patient compliance may also be achieved by the use of either injector pens (e.g the Novo Pin or Q-pen) or needle-free jet injectors (e.g. from Bioject, Mediject or Becton Dickinson). Prolonged zero-order or other precisely controlled release such as pulsatile release can also be achieved as needed using implantable pumps with delivery of the drug through a cannula into the synovial spaces. Examples include the subcutaneously implanted osmotic pumps available from ALZA, such as the ALZET osmotic pump.

Nasal delivery may be achieved by incorporation of the drug into bioadhesive particulate carriers (<200 μm) such as those comprising cellulose, polyacrylate or polycarbophil, in conjunction with suitable absorption enhancers such as phospholipids or acylcarnitines. Available systems include those developed by DanBiosys and Scios Nova.

A noteworthy attribute of the compounds of the present invention in contrast to those of various peptidic compounds referenced in the background section of this application is the demonstrated oral activity of the present compounds. Certain compounds have shown oral bioavailability in various animal models of up to 90–98%. Oral delivery may be achieved by incorporation of the drug into tablets, coated tablets, dragées, hard and soft gelatine capsules, solutions, emulsions or suspensions. Oral delivery may also be achieved by incorporation of the drug into enteric coated capsules designed to release the drug into the colon where digestive protease activity is low. Examples include the OROS-CT/Osmet™ and PULSINCAP™ systems from ALZA and Scherer Drug Delivery Systems respectively. Other systems use azo-crosslinked polymers that are degraded by colon specific bacterial azoreductases, or pH sensitive polyacrylate polymers that are activated by the rise in pH at the colon. The above systems may be used in conjunction with a wide range of available absorption enhancers.

Rectal delivery may be achieved by incorporation of the drug into suppositories.

The compounds of this invention can be manufactured into the above listed formulations by the addition of various therapeutically inert, inorganic or organic carriers well known to those skilled in the art. Examples of these include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like are also added, as required to assist in the stabilization of the formulation or to assist in increasing bioavailability of the active ingredient(s) or to yield a formulation of acceptable flavor or odor in the case of oral dosing.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of target enzyme which must be inhibited in order to treat the condition.

The matrix metalloprotease inhibitors of the invention are useful not only for treatment of the physiological conditions discussed above, but are also useful in such activities as purification of metalloproteases and testing for matrix metalloprotease activity. Such activity testing can be both in vitro using natural or synthetic enzyme preparations or in vivo using, for example, animal models in which abnormal destructive enzyme levels are found spontaneously (use of genetically mutated or transgenic animals) or are induced by administration of exogenous agents or by surgery which disrupts joint stability.

EXAMPLES

The following examples are offered for illustrative purposes only and are not intended, nor should they be construed, to limit the invention in any way.

General Procedures:

All reactions were performed in flame-died or oven-dried glassware under a positive pressure of argon and were stirred magnetically unless otherwise indicated. Sensitive liquids and solutions were transferred via syringe or cannula and were introduced into reaction vessels through rubber septa. Reaction product solutions were concentrated using a Buchi evaporator unless otherwise indicated.

Materials:

Commercial grade reagents and solvents were used without further purification except that diethyl ether and tetrahydrofuran were usually distilled under argon from benzophenone ketyl, and methylene chloride was distilled under argon from calcium hydride. Many of the specialty organic or organometallic starting materials and reagents were obtained from Aldrich, 1001 West Saint Paul Avenue, Milwaukee, Wis. 53233. Solvents are often obtained from EM Science as distributed by VWR Scientific.

Chromatography:

Analytical thin-layer chromatography (TLC) was performed on Analtech® pre-coated glass-backed silica gel GHLF 250 mm plates. Visualization of spots was effected by one of the following techniques: (a) ultraviolet illumination, (b) exposure to iodine vapor, (c) immersion of the plate in a 10% solution of phosphomolybdic acid in ethanol followed by heating, and (d) immersion of the plate in a 3% solution of p-anisaldehyde in ethanol containing 0.5% concentrated sulfuric acid followed by heating.

Column chromatography was performed using 230–400 mesh EM Science® silica gel.

Instrumentation:

Melting points (mp) were determined with a Thomas-Hoover melting point apparatus and are uncorrected.

Proton ($^1$H) nuclear magnetic resonance (NMR) spectra were measured with a General Electric GN-OMEGA 300 (300 MHz) spectrometer, and carbon thirteen ($^{13}$C) NMR spectra were measured with a General Electric GN-OMEGA 300 (75 MHz) spectrometer. Most of the compounds systhesized in the experiments below were analyzed by NMR, and the spectra were consistent with the proposed structures in each case.

Mass spectral (MS) data were obtained on a Kratos Concept 1-H spectrometer by liquid-cesium secondary ion (LCIMS), an updated version of fast atom bombardment (FAB). Most of the compounds systhesized in the experiments below were analyzed by mass spectroscopy, and the spectra were consistent with the proposed structures in each case.

General Comments:

For multi-step procedures, sequential steps are noted by numbers. Variations within steps are noted by letters. Dashed lines in tabular data indicates point of attachment.

Example 1—Preparation of Compound I

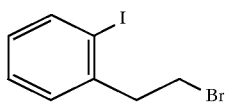

Step 1 A solution of o-iodophenylacetic acid (19.87 g, 75.83 mmol) in dry tetrahydrofuran (110 mL) was added dropwise over 41 min to a solution of borane in tetrahydrofuran (151 mL of 1M solution, ca. 151.0 mmol) which was cooled with an ice-water bath. The reaction was stirred at 0° to 10° C. for 2 h 15 min. After the reaction mixture was cooled to 0° C., it was quenched by cautious addition (frothing!) of 10 (vol.) % acetic acid in methanol over 20 min. Stirring was continued for 25 min before the reaction was concentrated on a rotary evaporator. The residue was dissolved in ethyl acetate and washed with saturated ammonium chloride followed by saturated sodium bicarbonate. The organics were dried ($Na_2SO_4$) and concentrated to a yellow oil (18.07 g) which was used in the next step without purification. Neat 2-(2-iodophenyl)ethanol (17.75 g, 71.55 mmol) was treated dropwise with phosphorous tribromide (3.5 mL, 36.85 mmol) over 6 min while the reaction vessel was placed in a water bath to modulate the exothermic reaction. Stirring was continued for 15 min at room temperature and then for 2 h while the mixture was heated in an oil bath at 100° C. The reaction was cooled to room temperature, diluted with ether and quenched carefully with water (frothing/exotherm!). The layers were separated, the organics were washed with saturated sodium bicarbonate and dried ($Na_2SO_4$). Concentration gave a yellow oil which was purified by Kugelrohr distillation (140° C./700 millitorr) to give a colorless oil (19.50 g, 62.71 mmol; 83% yield for above two steps). MS (EI) 310, 312 $[M]^+$.

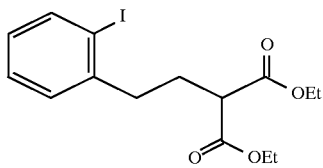

Step 2 A dry, 250 mL, round-bottomed flask was equipped with a stir bar and an argon inlet. The flask was charged with a suspension of sodium hydride (1.65 g of 95% NaH; ~65.1 mmol) in dry THF (25 mL). Diethyl malonate (9.99 g, 62.37 mmol) was added dropwise via syringe over 25 min. Fresh THF (10 mL) was used to wash the addition syringe into the reaction vessel. Stirring was continued for 10 min before rapidly adding the bromide from Step 1 (19.36 g, 62.26 mmol) in THF (20 mL). The addition syringe was washed (10 mL THF) into the reaction. The pale yellow solution was heated at reflux under argon with overnight stirring. The white suspension was partitioned between 10% HCl and ether. The ethereal layer was washed twice with $NaHCO_3$, dried ($Na_2SO_4$) and concentrated to an oil which was purified by bulb-to-bulb distillation: A forerun fraction (collected at 145° C., 700–900 millitorr) was discarded and the bulk distilled at 220° C. (500–600 millitorr). The bulk fraction was further purified by distilling off lower boiling material at 150° C. (300–500 millitorr) to leave the clean desired product in the pot (15.28 g, 39.16 mmol; 63% yield). TLC (developed twice in hexanes-ethyl acetate, 20:1): $R_f$=0.33.

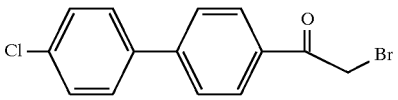

Step 3 A 2-L, three-necked, round-bottomed flask was equipped with a mechanical stirrer, a thermometer and an argon inlet. The flask was charged with a solution of 4-chlorobiphenyl (48.30 g, 0.256 mol) in dichloromethane (500 mL, freshly opened bottle). Bromoacetyl bromide (23 mL, ~53.3 g, ~0.26 mol) was added via syringe and the solution was cooled with an ice water bath to an internal temperature of 3° C. The thermometer was temporarily removed and $AlCl_3$ was added portionwise over 5 min. The internal temperature rose to 10° C. and white gas evolved from the opaque olive geeen reaction mixture. After 24 h of stirring, the reaction was quenched by cautiously pouring into cold 10% HCl (1 L). The organic layer became cloudy yellow green. Chloroform was added to help dissolve solids, but the organic layer never became transparent. The organics were concentrated on a rotary evaporator and were dried further under high vacuum. The crude product was a pale green solid (~82 g) which recrystallized from hot ethyl acetate to give 1-(2-bromoethanone)-4-(4-chlorophenyl)-benzene as brown needles (58.16 g). Concentration of the mother liquor followed by addition of hexanes delivered a second crop of crystals (11.06 g) which gave an NMR spectrum identical to that of the first crop. The total yield of the title product was 87%. TLC (hexanes-dichloromethane, 2:1): $R_f$=0.30.

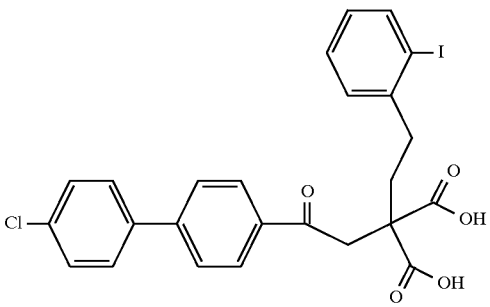

Step 4 A dry, 250 mL, round-bottomed flask was equipped with a stir bar and an argon inlet. The flask was charged with a suspension of sodium hydride (1.07 g of 95% NaH; ~42.4 mmol) in dry THF (100 mL) and was cooled with an ice-water bath. A solution of the malonate from Step 2 (15.25 g, 39.08 mmol) in THF (30 mL) was added dropwise over 30 min. Fresh THF (10 mL) was added by syringe to the reaction vessel and the cooling bath was removed. After the reaction stirred for 10 min, the bromomethyl ketone from Step 3 was added in a single portion. The orange mixtuxe was stirred under argon overnight while slowly warming to room temperature. The reaction mixture was cautiously added to 10% HCl. The layers were separated and the aqueous layer was extracted with ethyl acetate. The combined organics were washed sequentially with 10% HCl and saturated sodium bicarbonate. The combined organics were dried ($Na_2SO_4$) and concentrated to afford an orange-brown oil (24.41 g). This crude material was used in the next step without purification.

The crude oil (24.19 g, ~39.08 mmol) was dissolved in THF (150 mL) and absolute ethanol (100 mL). To this mixture was added NaOH solution (10 mL of 50 wt. % aqueous NaOH, ~0.125 mol) and the reaction was stirred under argon overnight at room temperature. The mixture was brought to pH~1 by adding 10% HCl and the cloudy, yellow solution was extracted with ethyl acetate. The combined organics were washed with brine, dried ($Na_2SO_4$) and concentrated to an orange foam (22.06 g). This material was used in the next step without purification. TLC (chloroform-methanol, 20:1 with trace amount of acetic acid): $R_f$=0.12.

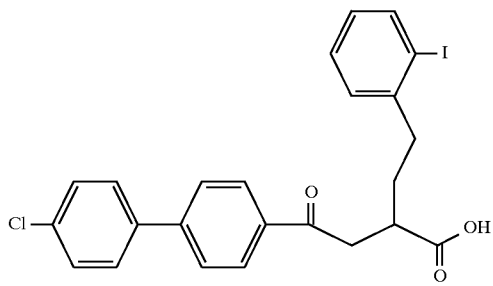

Step 5 The diacid product from step 4 (22.06 g) was dissolved in 1,4-dioxane (400 mL) and was held at reflux under argon overnight. Concentration gave the crude product as a yellow solid (19.50 g) which was recrystallized from chloroform to deliver two crops of the title compound Example 1 as a fluffy solid (11.55 g, 22.26 mmol; 57% overall yield) after overnight drying in a vacuum oven at 66° C. TLC (chloroform-methanol, 20:1 with trace amount of acetic acid): $R_f$=0.54.

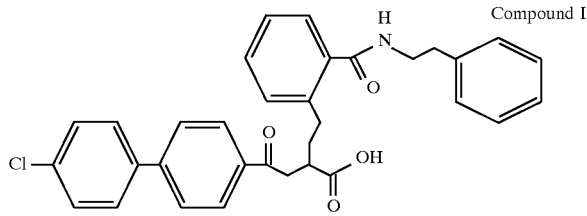

Step 6 A portion of the acid from Step 5 (405.7 mg, 0.78 mmol) was dissolved in dimethylsulfoxide (3.0 mL). Triethyl amine (0.34 mL) was added followed by palladium (II) acetate (20.3 mg, 0.09 mmol), 1,3-bis(diphenylphosphino) propane (35.2 mg, 0.085 mmol) and phenethylamine (1.42 g, 11.7 mmol). Carbon monoxide was bubbled through the solution for five minutes. The solution was placed under a carbon monoxide atmosphere and was heated in an oil bath at 70°–75° C. overnight. The mixture was cooled to room temperature, diluted with ethyl acetate (50 mL) and washed with 10% HCl followed by water. The aqueous phase was back-extracted with ethyl acetate and the combined organics were dried ($MgSO_4$) and concentrated to a yellow-orange solid. Purification by flash chromatography (chloroform-methanol, 95:5) gave an off-white solid which was recrystallized from ethyl acetate hexanes to give the title compound (219.7 mg, 0.41 mmol; 53% yield). Anal. (for $C_{33}H_{30}NO_4Cl$) C: calcd, 73.39; found, 73.11. H: calcd, 5.60; found, 5.40. N: calcd, 2.59; found, 2.32.

The examples in Table I were prepared by the palladium-mediated carbonylation method of Example 1 with the appropriate amine in place of phenethyl amine. Furthermore, the requisite isomeric iodide precursors were prepared by the method of Example 1 using m- or p-iodophenylacetic acid as starting material.

TABLE I

| Compound | $R^{25}$ | ISOMER | M.P. (°C.) |
|---|---|---|---|
| II | –(CH$_2$)$_2$–(2-morpholinocarbonylphenyl) | R,S | 83–87 |
| III | –(CH$_2$)$_2$–(2-(N-benzylcarbamoyl)phenyl) | R,S | 174.5–175.5 |
| IV | –(CH$_2$)$_2$–(2-(N-(2-phenylethyl)carbamoyl)phenyl) | R,S | 166–167 |

TABLE I-continued

[Structure: 4-chlorobiphenyl-4'-yl-C(O)-CH2-CH(R25)-C(O)OH]

| Compound | R25 | ISOMER | M.P. (°C.) |
|---|---|---|---|
| V | 2-(piperidin-1-ylcarbonyl)phenyl-(CH2)2— | R,S | 78.5–80 |
| VI | 2-(N-isobutylcarbamoyl)phenyl-(CH2)2— | R,S | 66–69 |
| VII | 2-[N-(2-ethoxycarbonylethyl)carbamoyl]phenyl-(CH2)2— | R,S | 143.5–146 |
| VIII | 2-[N-(ethoxycarbonylmethyl)carbamoyl]phenyl-(CH2)2— | R,S | 69–72 |
| IX | 2-[N-methyl-N-(ethoxycarbonylmethyl)carbamoyl]phenyl-(CH2)2— | R,S | 110–113 |
| X | 3-(morpholin-4-ylcarbonyl)phenyl-(CH2)2— | R,S | 116–118 |
| XI | 3-(piperidin-1-ylcarbonyl)phenyl-(CH2)2— | R,S | 209–210 |

TABLE I-continued
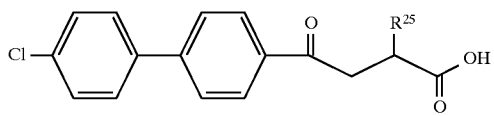
| Compound | R²⁵ | ISOMER | M.P. (°C.) |
|---|---|---|---|
| XII | 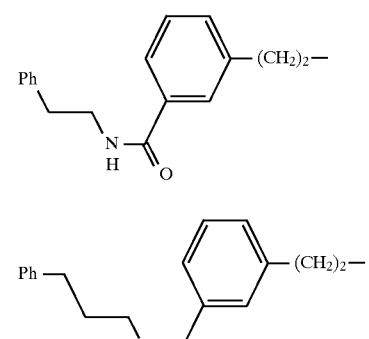 | R,S | 80–83 |
| XIII | 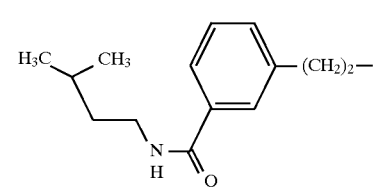 | R,S | 66–69 |
| XIV | 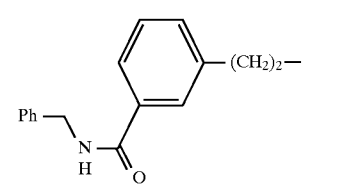 | R,S | 76–79 |
| XV | 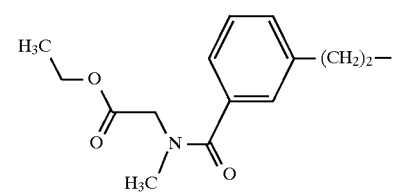 | R,S | 79–83 |
| XVI | 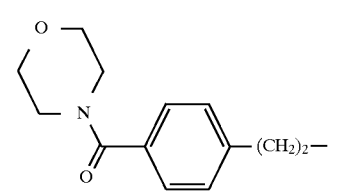 | R,S | 88–90 |
| XVII | 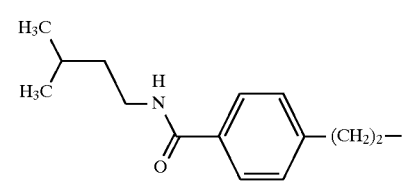 | R,S | 190–191 |
| XVIII |  | R,S | 189.5–190.5 |

TABLE I-continued

[Structure: 4'-chlorobiphenyl-C(O)-CH2-CH(R25)-C(O)OH]

| Compound | R25 | ISOMER | M.P. (°C.) |
|---|---|---|---|
| XIX | ethoxycarbonylmethyl-NH-C(O)-C6H4-(CH2)2– | R,S | 184.5–185 |
| XX | phenethyl-NH-C(O)-C6H4-(CH2)2– | R,S | 196.5–197 |
| XXI | piperidinyl-N-C(O)-C6H4-(CH2)2– | R,S | 180.5–181 |

Example 22—Preparation of Compound XXII

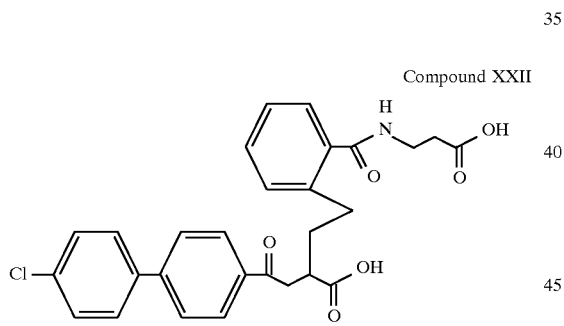

Compound XXII

The acid from Example 7 (200 mg, 0.37 mmol) was dissolved in ethanol (15 mL) and was treated with 1N NaOH (1.8 mL, 1.8 mmol). The mixture was stirred at room temperature over the weekend. The reaction was concentrated to dryness and the residue was partitioned between chloroform and 10% HCl. The layers were separated and the aqueous phase was extracted again with chloroform. The combined organics were dried (Na$_2$SO$_4$) and concentrated to an off-white solid. The crude product was recrystallized from ethanol-hexane to give the product as off-white crystals (65 mg, 0.128 mmol; 35% yield). MP 189.5°–190.5° C.

Example 23—Preparation of Compound XXIII

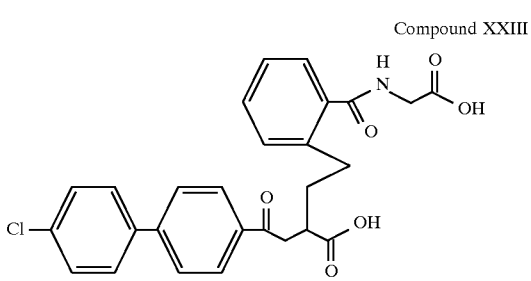

Compound XXIII

The acid from Example 8 (180 mg, 0.34 mmol) was saponified according to the general method of Example 22 to give the diacid product as a yellow solid (142 mg, 85% yield). MP 71°–75° C.

Example 24—Preparation of Compound XXIV

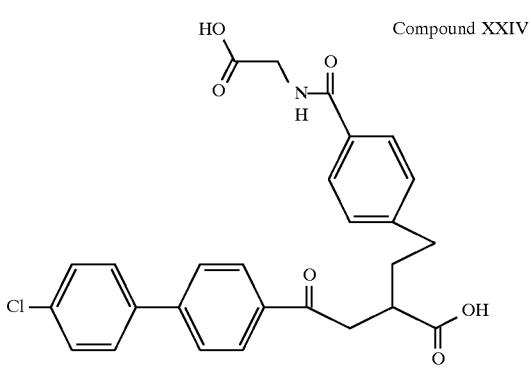

Compound XXIV

The acid from Example 19 (104 mg, 0.199 mmol) was saponified according to the general method of Example 22 to give the diacid product as colorless crystals (79 mg, 80% yield). MP 164.5°–165.5° C.

Example 25—Preparation of Compound XXV

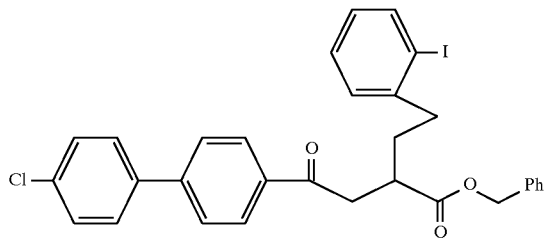

Step 1 A sample of the iodo acid from Example 1, Step 5 (1.0 g, 1.93 mmol) was suspended in dry dichloromethane (20 mL). To the stirred suspension was added benzyl alcohol (0.44 mL, 4.05 mmol), DCC (0.6 g, 2.89 mmol) and DMAP (50 mg, 0.39 mmol). The yellow suspension was stirred overnight at room temperature. The mixture was diluted with hexanes (60 mL) and water (5 mL). The mixture was stirred and filtered and the filter cake was washed with hexanes. The organics were separated, dried (MgSO$_4$) and concentrated to an oil. Flash chromatography (gradient elution, hexane-ethyl acetate, 9:1 to 1:1) gave the purified ester as an oil (0.95 g, 1.56 mmol; 81% yield). TLC (hexanes-ethyl acetate, 1:1): R$_f$=0.64.

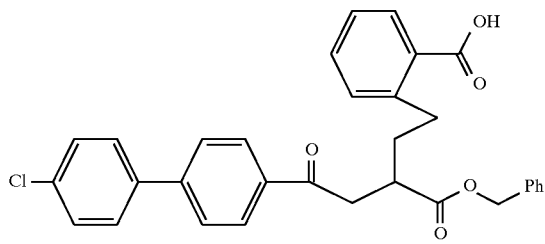

Step 2 The iodo ester from Step 1 (0.910 g, 1.49 mmol) was subjected to the palladium-mediated carbonylation method of Example 1 with water in place of phenethyl amine to give the half acid ester product (475 mg, 0.90 mmol; 61% yield). MS (FAB-LSIMS) 527[M+H]$^+$

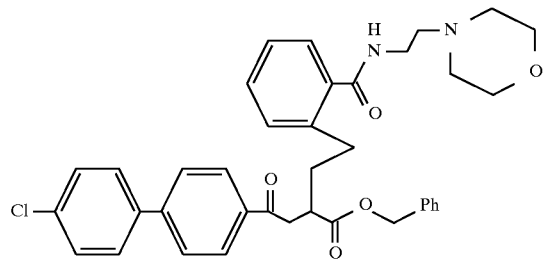

Step 3 The half acid ester from Step 2 (0.46 g, 0.87 mmol) was dissolved in dichloromethane (8 mL). To the solution was added 4-(2-aminoethyl)morpholine (0.13 g, 0.96 mmol) and 1-hydroxybenzotriazole (0.12 g, 0.87 mmol). The flask was washed down with dichloromethane (2 mL) and cooled in an ice bath. 4-Methylmorpholine was added (97 mg, 0.96 mmol) followed by 1-(3-dimethylaminopropyl)-3-ethyl-carbodiimide hydrochloride (0.18 g, 0.96 mmol). The yellow solution was warned to room temperature with overnight stirring. The mixture was diluted with dichloromethane (40 mL) and washed with water. The aqueous layers were back-extracted with dichloromethane. The combined organics were dried (Na$_2$SO$_4$) and concentrated. Purification by flash chromatography (chloroform-methanol, 95:5) gave the product as a pale yellow oil (0.438 g, 0.685 mmol; 78% yield). TLC (chloroform-methanol, 9:1): R$_f$=0.70.

Compound XXV

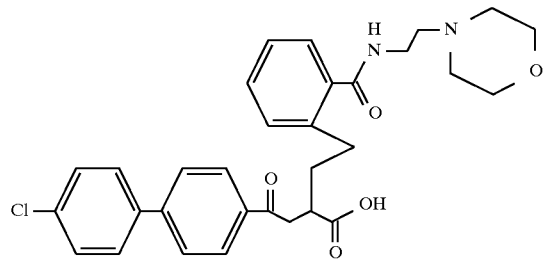

Step 4. The acid from Step 3 (0.15 g, 0.47 mmol) was saponified according to the general method of Example 22 to give the product as cream colored foam (65.2 mg, 52%). MP 127°–129° C.

Example 26—Preparation of Compound XXVI

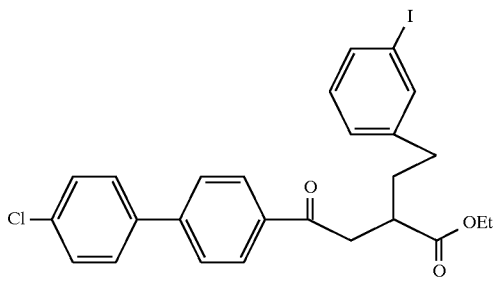

Step 1 The meta-iodo isomer of Example 1, Step 5 (i.e., prepared according to the procedure of Example 1 beginning with m-iodophenyl acetic acid; 2.0 g, 3.86 mmol) was dissolved in 1,2-dichloroethane (8 mL). To the solution was added ethanol (0.68 mL, 11.57 mmol) and several drops of concentrated sulfuric acid. The solution was held at reflux overnight. The mixture was cooled, loaded onto a silica column and flash chromatographed (hexanes-ethyl acetate, 3:1) to give the product as a yellow oil (2.142 g) which retained solvent by proton NMR. TLC (chloroform-methanol, 10:1): R$_f$=0.91.

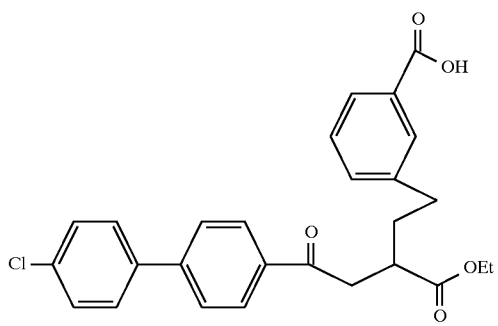

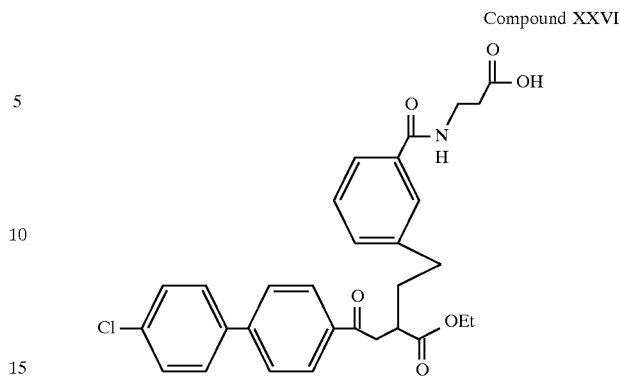

Step 2 The iodo ester from Step 1 (2.1 g, 3.84 mmol) was subjected to the palladium-mediated carbonylation method of Example 1 with water in place of phenethyl amine to give the half acid ester product (1.1 g, 2.37 mmol; 62% yield). TLC (1:1 hexane-ethyl acetate with 1% acetic acid): $R_f$=0.70.

Step 3 The half acid ester from Step 2 was converted to Example 26 using b-alanine ethyl ester in the general method of Example 25. MP 261°–261° C.

The examples in Table II were prepared by the general multi-step method of Example 25 starting with the appropriate iodo acid and amine precursors.

TABLE II

| COMPOUND | $R^{25}$ | ISOMER | M.P. (°C.) |
|---|---|---|---|
| XXVII | O⌒N−CH₂CH₂−NH−C(O)−C₆H₄−(CH₂)₂− (morpholinoethylamido-phenyl ethyl) | R,S | 182–185 |
| XXVIII | (CH₃)₂N−CH₂CH₂−N(CH₃)−C(O)−C₆H₄−(CH₂)₂− | R,S | 78–80 |
| XXIX | O⌒N−CH₂CH₂−NH−C(O)−C₆H₄−(CH₂)₂− (para isomer) | R,S | 114–125 |

Example 30—Preparation of Compound XXX

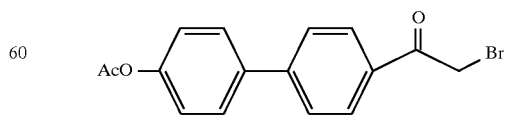

Step 1 A one-necked, 1000-mL, round-bottomed flask equipped with an argon inlet adapter was charged with 500 mL CH₂Cl₂, 4-phenylphenol acetate (50.0 g, 235 mmol), bromoacetyl bromide (73.2 g, 31.6 mL, 363 mmol) and cooled to 0° C. while aluminum trichloride (94.2 g, 707 mmol) was added in small portions ca. over 5 min. The resulting mixture was stirred for 30 min at 0° C. and 12 h at room temperature. The reaction mixture was added to a cold 10% HCl solution (500 mL), and extracted three times with 200-mL portions of ethyl acetate. The organic phase was dried over $MgSO_4$, filtered, and concentrated to provide a black solid. Recrystallization from ethyl acetate-hexanes afforded 44.3 g (56%) of the desired compound as a brown solid. TLC (hexanes-ethyl acetate, 9:1) $R_f=0.14$.

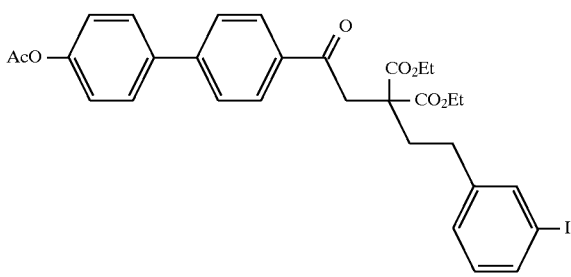

Step 2 The desired compound was synthesized from the product of Step 1 above by the general procedure in Example 1. TLC (hexanes-ethyl acetate, 3:1) $R_f=0.49$.

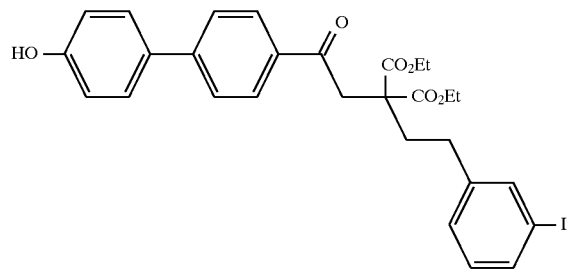

Step 3 A tetrahydrofuran (400 mL) and ethanol (50 mL) solution of the product from Step 2 (18.4 g) was treated with $K_2CO_3$ and stirred under argon at room temperature overnight. Because a significant amount of starting material remained, the volume of the reaction was reduced by one half and additional $K_2CO_3$ (12 g) was added. The reaction was complete after 3 h. The reaction was concentrated and acidified with 10% HCl. The product was extracted with ethyl acetate, dried ($Na_2SO_4$) and concentrate to a brown oily residue. Purification by flash chromatography (hexanes-ethyl acetate, 3:1) gave the product as a yellow oil (14.8 g; 86%). TLC (hexanes-ethyl acetate, 3:1) $R_f=0.20$.

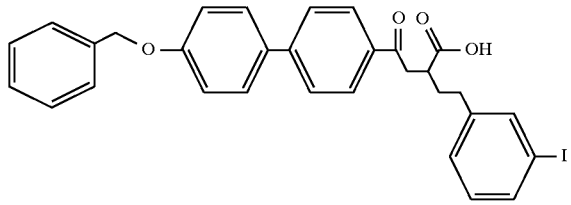

Step 4 A suspension of NaH (95% by weight, 143 mg, ~5.95 mmol) in dry DMF (10 mL) was cooled with an ice-water bath and treated with a solution of the phenol from Step 3 (3.4 g, 5.66 mmol) in dry DMF (20 mL). The mixture was warmed to room temperature and benzyl bromide (3.4 mL, ~28.3 mmol) was added in a single portion. The flask was stirred at room temperature overnight. The mixture was diluted with 10% HCl and extracted with ethyl acetate. The organics were dried ($MgSO_4$) and concentrated to a yellow oil. Flash chromatography (gradient elution, hexanes-ethyl acetate, 9:1 to 3:2) gave the intermediate diester (3.32 g). This material was dissolved in a mixture of THF (25 mL), ethanol (100 mL) and 1N NaOH (22 mL) and the solution was stirred overnight. The reaction mixture was concentrated and the residue was partitioned between 10% HCl and ethyl acetate. The organics were dried ($Na_2SO_4$) and concentrated to a white solid (2.51 g). This diacid was dissolved in 1,4-dioxane (250 mL) and the solution was held at reflux overnight. The solution was cooled and concentrated to a yellow-white solid (2.36 g). Recrystallization from ethyl acetate gave pale yellow crystals (1.77 g). MP 173°–174° C. TLC (hexanes-ethyl acetate, 3:1 with a trace of acetic acid) $R_f=0.43$.

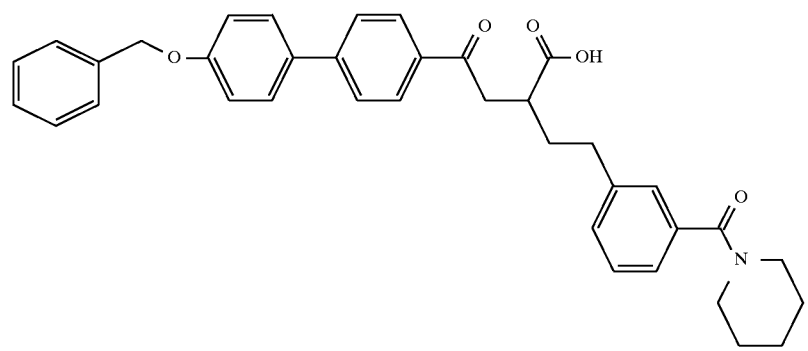

Compound XXX

Step 5. Example 30 was prepared by the palladium-mediated carbonylation method of Example 1 with piperidine as the nucleophile. MP 100°–102.5° C.

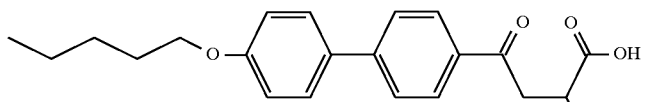

Example 31—Preparation of Compound XXXI

Example 31 was prepared by the general procedure of Example 30 using iodopentane in the alkylation step and piperidine as the nucleophile in the palladium-mediated carbonylation. MP 105.5°–107.5° C.

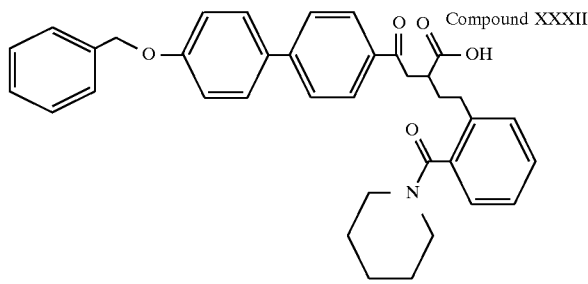

Example 32—Preparation of Compound XXXII

Example 32 was prepared by the general procedure of Example 30 using the appropriate isomeric iodo precursor. MP 168°–169° C.

Example 33

Biological Assays of Invention Compounds
P218 Quenched Fluorescence Assay for MMP Inhibition:

The P218 quenched fluorescence assay (Microfluorometric Profiling Assay) is a modification of that originally described by Knight, et al., FEBS Lett. 296, 263, 1992 for a related substance and a variety of matrix metalloproteinases (MMPs) in cuvettes. The assay was run with each invention compound and the three MMPs, Mmp-3, MMP-9 and MMP-2, analyzed in parallel, adapted as follows for a 96-well microtiter plate and a Hamilton AT® workstation.

P218 Fluorogenic Substrate:

P218 is a synthetic substrate containing a 4-acetyl-7-methoxycoumarin (MCA) group in the N-terminal position and a 3-[2, 4-dinitrophenyl]-L-2,3-diaminopropionyl (DPA) group internally. This is a modification of a peptide reported by Knight (1992) that was used as a substrate for matrix metalloproteinases. Once the P218 peptide is cleaved (putative clip site at the Ala-Leu bond), the fluorescence of the MCA group can be detected on a fluorometer with excitation at 328 nm and emission at 393 nm. P218 is currently being produced BACHEM exclusively for Bayer. P218 has the structure:

H-MCA-Pro-Lys-Pro-Leu-Ala-Leu-DPA-Ala-Arg-NH2
(MW 1332.2)

Recombinant Human CHO Stromelysin (MMP-3)

Recombinant Human CHO Pro-MMP-3: Human CHO pro-stromelysin-257 (pro-MMP-3) was expressed and purified as described by Housley, et al., J. Biol. Chem. 268, 4481, 1993.

Activation of Pro-MMP-3: Pro-MMP-3 at 1.72 μM (100 μg/mL) in 5 mM Tris at pH 7.5, 5 mM CaCl$_2$, 25 mM NaCl, and 0.005% Brij-35 (MMP-3 activation buffer) was activated by incubation with TPCK (N-tosyl-(L)-phenylalanine chloromethyl ketone) trypsin (1:100 w/w to pro-MMP-3) at 25° C. for 30 min. The reaction was stopped by addition of soybean trypsin inhibitor (SBTI; 5:1 w/w to trypsin concentration). This activation protocol results in the formation of 45 kDa active MMP-3, which still contains the C-terminal portion of the enzyme.

Preparation of Human Recombinant Pro-Gelatinase A (MMP-2):

Recombinant Human Pro-MMP-2: Human pro-gelatinase A (pro-MMP-2) was prepared using a vaccinia expression system according to the method of Fridman, et al., J. Biol. Chem. 267, 15398, 1992.

Activation of Pro-MMP-2: Pro-MMP-2 at 252 mg/mL was diluted 1:5 to a final concentration of 50 μg/mL solution in 25 mM Tris at pH 7.5, 5 mM CaCl$_2$, 150 mM NaCl, and 0.005% Brij-35 (MMP-2 activation buffer). p-Aminophenylmercuric acetate (APMA) was prepared in 10 mM (3.5 mg/mL) in 0.05 NaOH. The APMA solution was added at 1/20 the reaction volume for a final AMPA concentration of 0.5 mM, and the enzyme was incubated at 37° C. for 30 min. Activated MMP-2 (15 mL) was dialyzed twice vs. 2 L of MMP-2 activation buffer (dialysis membranes were pre-treated with a solution consisting of 0.1% BSA in MMP-2 activation buffer for 1 min. followed by extensive H$_2$O washing). The enzyme was concentrated on Centricon concentrators (concentrators were also pre-treated a solution consisting of 0.1% BSA in MMP-2 activation buffer for 1 min. followed by washing with H$_2$O, then MMP-2 activation buffer) with re-dilution followed by re-concentration repeated twice. The enzyme was diluted to 7.5 mL (0.5 times the original volume) with MMP-2 activation buffer.

Preparation of Human Recombinant Pro-Gelatinase B (MMP-9):

Recombinant Human Pro-MMP-9: Human pro-gelatinase B (pro-MMP-9) derived from U937 cDNA as described by Wilhelm, et al. J. Biol. Chem. 264, 17213, 1989 was expressed as the full-length form using a baculovirus protein expression system. The pro-enzyme was purified using methods previously described by Hibbs, et al. J. Biol. Chem. 260, 2493, 1984.

Activation of Pro-MMP-9: Pro-MMP-2 20 μg/mL in 50 mM Tris at pH 7.4, 10 mM CaCl$_2$, 150 mM NaCl, and 0.005% Brij-35 (MMP-9 activation buffer) was activated by incubation with 0.5 mM p-aminophenylmercuric acetate (APMA) for 3.5 h at 37° C. The enzyme was dialyzed against the same buffer to remove the APMA.

Instrumentation:

Hamilition Microlab AT Plus: The MMP-Profiling Assay is performed robotically on a Hamilton MicroLab AT Plus®. The Hamilton is programmed to: (1) serially dilute up to 11 potential inhibitors automatically from a 2.5 mM stock in 100% DMSO; (2) distribute substrate followed by inhibitor into a 96 well Cytofluor plate; and (3) add a single enzyme to the plate with mixing to start the reaction. Subsequent plates for each additional enzyme are prepared automatically by beginning the program at the substrate addition point, remixing the diluted inhibitors and beginning the reaction by addition of enzyme. In this way, all MMP assays were done using the same inhibitor dilutions.

Millipore Cytofluor II. Following incubation, the plate was read on a Cytofluor II fluorometric plate reader with excitation at 340 nM and emission at 395 nM with the gain set at 80.

Buffers:

Microfluorometric Reaction Buffer (MRB): Dilution of test compounds, enzymes, and P218 substrate for the microfluorometric assay were made in microfluorometric reaction buffer consisting of 50 mM 2-(N-morpholino) ethanesulfonic acid (MES) at pH 6.5 with 10 mM $CaCl_2$, 150 mM NaCl, 0.005% Brij-35 and 1% DMSO.

Methods:

MMP Microfluorometric Profiling Assay. The assay is done with a final substrate concentration of 6 $\mu$M P218 and approximately 0.5 to 0.8 nM MMP with variable drug concentrations. The Hamilton is programmed to serially dilute up to 11 compounds from a 2.5 mM stock (100% DMSO) to 10× the final compounds concentrations in the assay. Initially, the instrument delivers various amounts of microfluoromentric reaction buffer (MRB) to a 96 tube rack of 1 ml Marsh dilution tubes. The instrument then picks up 20 $\mu$l of inhibitor (2.5 mM) from the sample rack and mixes it with a buffer in row A of the Marsh rack, resulting in a 50 $\mu$M drug concentration. The inhibitors are then serially diluted to 10, 5, 1, 0.2, 0.05 and 0.01 $\mu$M. Position 1 on the sample rack contains only DMSO for the "enzyme-only" wells in the assay, which results in no inhibitor in column 1, rows A through H. The instrument then distributes 107 $\mu$l of P218 substrate (8.2 $\mu$M in MRB) to a single 96 well cytofluor microtiter plate. The instrument re-mixes and loads 14.5 $\mu$l of diluted compound from rows A to G in the Marsh rack to corresponding rows in the microtiter plate. (Row H represents the "background" row and 39.5 $\mu$l of MRB is delivered in placed of drug or enzyme). The reaction is started by adding 25 $\mu$l of the appropriate enzyme (at 5.86 times the final enzyme concentration) from a BSA treated reagent reservoir to each well, excluding Row H, the "background" row. (The enzyme reservoir is pretreated with 1% BSA in 50 mM Tris, pH 7.5 containing 150 mM NaCl for 1 hour at room temp., followed by extensive $H_2O$ washing and drying at room temp.).

After addition and mixing of the enzyme, the plate is covered and incubated for 25 min. at 37° C. Additional enzymes are tested in the same manner by beginning the Hamilton program with the distribution of P218 substrate to the microtiter plate, followed by re-mixing and distribution of the drug from the same Marsh rack to the microtiter plate. The second (or third, etc.) MMP to be tested is then distributed from a reagent rack to the microtiter plate with mixing, prior to covering and incubation. This is repeated for all additional MMP's to be tested.

IC50 and Ki Determination in Microfluorometric Assay: Data generated on the Cytofluor II is copied from an exported ".CSV" file to a master Excel spreadsheet. Data from several different MMPs (one 96 well plate per MMP) were calculated simultaneously. The percent inhibition is determination for each drug concentration by comparing the amount of hydrolysis (fluorescence units generated over 25 minutes of hydrolysis) of wells containing compound with the "enzyme only" wells in column 1. Following subtraction of the background the percent inhibition was calculated as:

$$((\text{Control values}-\text{Treated values})/\text{Control values})\times 100$$

Percent inhibitions were determined for inhibitor concentrations of 5, 1, 0.5, 0.1, 0.02, 0.005 and, 0.001 $\mu$M of drug. Linear regression analysis of percent inhibition versus log inhibitor concentration was used to obtain $IC_{50}$ values.

$K_i$'s were calculated automatically for each enzyme tested based upon the equation:

$$K_i=((K_m \times IC_{50})/(K_m+[S]))$$

where [S]=substrate concentration=6 $\mu$M. This is the method of Williams, et at., *Methods Enzym.* 63, 437, 1979.

TABLE III

| COMPOUND | MMP-3 $K_i$ (nM) | MMP-9 $K_i$ (nM) | MMP-2 $K_i$ (nM) |
|---|---|---|---|
| I | 127 | 173 | 41.1 |
| II | 122 | 323 | 12.1 |
| III | 174 | 475 | 60.3 |
| IV | 175 | 246 | 68.7 |
| V | 54.7 | 146 | 13.8 |
| VI | 214 | 431 | 58.1 |
| VII | 131 | 478 | 27.1 |
| VIII | 165 | 806 | 56.8 |
| IX | 43.6 | 254 | 17.5 |
| X | 73.8 | 251 | 26.1 |
| XI | 34.4 | 58.1 | 10.3 |
| XII | 450 | 2650 | 125 |
| XIII | 236 | 552 | 157 |
| XIV | 308 | 707 | 110 |
| XV | 364 | 493 | 104 |
| XVI | 24.8 | 137 | 9.86 |
| XVII | 236 | 606 | 53.6 |
| XVIII | 677 | 452 | 137 |
| XIX | 376 | 423 | 82.3 |
| XX | — | 2000 | 446 |
| XXI | 242 | 806 | 84.1 |
| XXII | 166 | 1130 | 63.5 |
| XXIII | 259 | 1590 | 96.0 |
| XXIV | 293 | 915 | 82.4 |
| XV | 371 | 744 | 51.4 |
| XVI | 178 | 706 | 76.6 |
| XVII | 353 | 786 | 48.0 |
| XVIII | 42.8 | 201 | 24.1 |
| XXIX | 465 | 449 | 81.4 |
| XXX | 12.5 | 102 | 4.44 |
| XXXI | 35.8 | 373 | 17.0 |
| XXXII | 14.8 | 167 | 13.0 |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A matrix metalloprotease-inhibiting compound having the general formula:

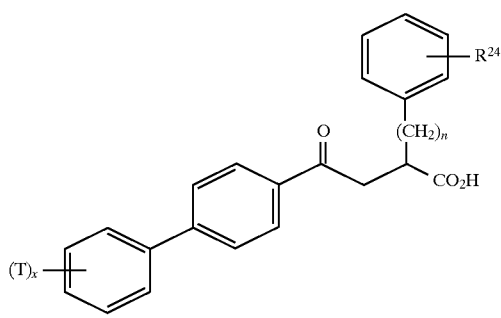

wherein
- T represents halogen, benzyloxy, or alkoxy of 1–5 carbon atoms,
- x is 1 or 2;
- n is an integer of 1–5, and
- R²⁴ is selected from the group consisting of

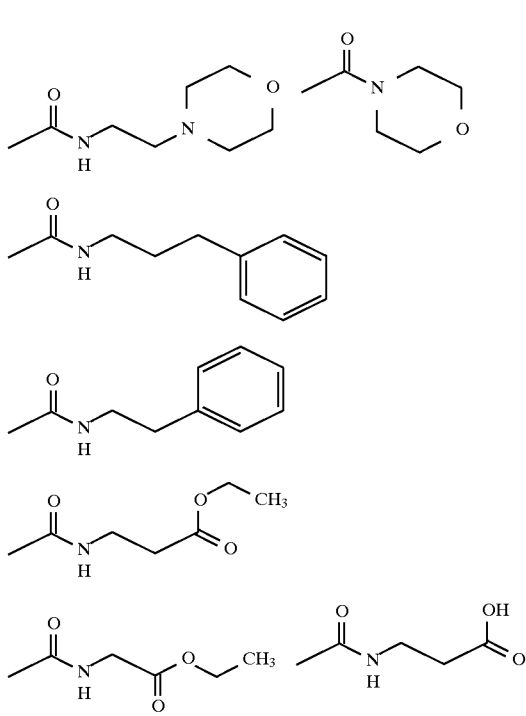

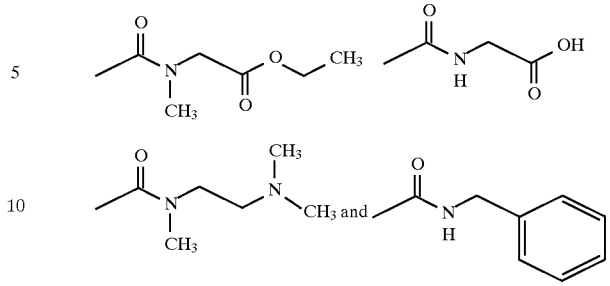

and pharmaceutically acceptable salts thereof.

2. A composition having matrix metalloprotease inhibitory activity, comprising a compound of claim 1 and a pharmaceutically acceptable carrier.

3. A method of inhibiting matrix metalloprotease activity in a mammal comprising administration of an effective amount matrix metalloprotease inhibitor compound of claim 1 to said mammal.

4. The method of claim 3 wherein said mammal is a human.

5. A method of treating a mammal comprising administering to the mammal a matrix metalloprotease inhibiting amount of a compound according to claim 1 sufficient to:

(a) alleviate the effects of osteoarthritis, rheumatoid arthritis, septic arthritis, periodontal disease, corneal ulceration, proteinuria, aneurysmal aortic disease, dystrophobic epidermolysis, bullosa, conditions leading to inflammatory responses, osteopenias mediated by MMP activity, tempero mandibular joint disease, demyelating diseases of the nervous system;

(b) retard tumor metastasis or degenerative cartilage loss following traumatic joint injury;

(c) reduce coronary thrombosis from athrosclerotic plaque rupture; or (d) effect birth control.

6. The method of claim 5 wherein the effect is alleviation of osteoarthritis.

7. The method of claim 5 wherein the effect is retardation of tumor metastasis.

* * * * *